United States Patent
Ullman et al.

(10) Patent No.: US 6,482,590 B1
(45) Date of Patent: Nov. 19, 2002

(54) METHOD FOR POLYNUCLEOTIDE AMPLIFICATION

(75) Inventors: Edwin F. Ullman, Atherton, CA (US); Alla Lishanski, San Jose, CA (US); Nurith Kurn, Palo Alto, CA (US)

(73) Assignee: Aventis Behring GmbH, Marburg (DE)

(*) Notice: Subject to any disclaimer, the term of this patent is extended or adjusted under 35 U.S.C. 154(b) by 0 days.

(21) Appl. No.: 08/965,492

(22) Filed: Nov. 6, 1997

Related U.S. Application Data

(60) Provisional application No. 60/033,137, filed on Dec. 20, 1996.

(51) Int. Cl.[7] .............. C12Q 1/68; C12P 19/34; C07H 21/04
(52) U.S. Cl. .............. 435/6; 435/91.2; 435/91.1; 536/23.1
(58) Field of Search .............. 435/91.2, 91.1; 536/23.1

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/435 |
| 4,800,159 A * | 1/1989 | Mullis et al. | 435/172.3 |
| 4,965,188 A | 10/1990 | Mullis et al. | 435/91 |
| 4,994,368 A | 2/1991 | Goodman et al. | 435/6 |
| 5,008,182 A | 4/1991 | Sninsky et al. | 435/91.1 |
| 5,043,272 A | 8/1991 | Hartley | 435/91 |
| 5,218,088 A * | 6/1993 | Gorenstein et al. | 536/25.34 |
| 5,436,143 A * | 7/1995 | Hyman | 435/91.2 |
| 5,508,178 A | 4/1996 | Rose et al. | 435/91.1 |
| 5,573,907 A | 11/1996 | Carrino et al. | 435/6 |
| 5,591,609 A | 1/1997 | Auerbach | 435/91.2 |
| 5,614,389 A | 3/1997 | Auerbach | 435/91.2 |
| 5,677,152 A | 10/1997 | Birch et al. | 435/91.2 |
| 5,679,512 A | 10/1997 | Laney et al. | 435/6 |
| 5,679,553 A | 10/1997 | Van Gemen et al. | 435/91.2 |
| 5,733,733 A | 3/1998 | Auerbach | 435/6 |
| 5,747,255 A | 5/1998 | Brenner | 435/6 |
| 5,753,439 A | 5/1998 | Smith et al. | 435/6 |
| 5,763,594 A * | 6/1998 | Hiatt et al. | 536/25.3 |
| 5,766,849 A * | 6/1998 | McDonough et al. | 435/6 |
| 6,294,336 B1 * | 9/2001 | Boyce-Jacino et al. | 435/6 |

FOREIGN PATENT DOCUMENTS

| | | | |
|---|---|---|---|
| EP | 549107 A1 | 6/1993 | C12Q/1/68 |
| EP | 439182 | 4/1996 | C12Q/1/68 |
| EP | 744470 A1 | 11/1996 | C12Q/1/68 |
| JP | 7000198 | 1/1995 | C12Q/1/68 |
| WO | WO 86/06412 | 11/1986 | C12Q/1/68 |
| WO | WO 9602672 | 2/1996 | C12Q/1/68 |
| WO | WO 9728279 | 8/1997 | C12Q/1/68 |

OTHER PUBLICATIONS

Arne Skerra et al., Phosphorothioate primers improve the amplification of DNA sequences by DNA polymerases with proofreading activity, Nucleic Acids Research, vol. 20, No. 14, pp. 3551–3554, 1992 Oxford University Press.

Birch et al; *Simplified hot start PCR*, Nature, 381:445–446, May 30, 1996.

Noronha et a *Amplimers with 3'–Terminal Phosphorothioate Linkages Resist Degradation by Vent Polymerase and Reduce Tag Polymerase Mispriming*; PCR Methods and Applications, 2: 131–136; 1992.

Chou, et al., *Prevention of pre–PCR mis–priming and primer dimerization improves low–copy–number amplifications*, Nucleic Acids Research, 20 No. 7: 1717–1723, 1992.

Barnes, W.M., *PCR amplificatin of up to 35–kb DNA with high fidelity and high yield from λ bacteriophage templates*, Proc. Nat. Acad. Sci USA, 91:2216–2220, 1994.

Saiki, et al., *Enzymatic Amplification of β–Globin Genomic Sequences and Restriction Site Analysis for Diagnosis of Sickle Cell Anemia*; Science, 230:1350–1354, 1985.

Saiki, et al., *Primer–Directed Enzymatic Amplification of DNA with a Thermostable DNA Polymerase*, Science, 239:487–491, 1988.

Nickel, et al., *Interactions of Azidothymidine Triphosphate with the Cellular DNA Polymerases α, δ, and ε and with DNA Primase*; Journal of Biological Chemistry, 267:848–854, 1992.

(List continued on next page.)

*Primary Examiner*—Gary Benzion
*Assistant Examiner*—Joyce Tung
(74) *Attorney, Agent, or Firm*—McDonnell Boehnen Hulbert & Berghoff

(57) ABSTRACT

The present invention relates to a method for selectively extending an oligonucleotide primer along a specific target polynucleotide sequence in a mixture of polynucleotides. Selective extension is achieved by controlling the concentration of the oligonucleotide primer by forming the oligonucleotide in situ by degrading the 3'-end of a modified oligonucleotide. The method comprises providing in combination the mixture of polynucleotides and the modified oligonucleotide having a 3'-end that is not extendable along any polynucleotide and extending the oligonucleotide primer selectively along the specific target polynucleotide sequence by controlling the degradation of the 3'-end of the modified oligonucleotide. In this way extension of the oligonucleotide primer along polynucleotides other than the specific target polynucleotide sequence is substantially reduced or avoided. In another aspect the invention is an improvement in a method for amplifying a target polynucleotide sequence. The method comprises combining the target polynucleotide sequence with reagents for amplifying the target polynucleotide sequence and subjecting the combination to conditions wherein the target polynucleotide sequence is amplified. The reagents comprise an oligonucleotide primer and a polymerase. The improvement comprises deriving the oligonucleotide primer from a modified oligonucleotide having a portion that hybridizes to the target polynucleotide sequence except for the 3'-end thereof, which has at least one nucleotide analog that is incapable of hybridizing to a polynucleotide. Kits for carrying out the above methods are also disclosed.

35 Claims, 4 Drawing Sheets

OTHER PUBLICATIONS

Moran, et al., *Non–hydrogen bonding 'terminator' nucleosides increase the 3'–end homogeneity of enzymatic RNA and DNA synthesis*, Nucleic Acids Research, 24 No. 11:2044–2052, 1996.

Solomon, et al., *Chemical Synthesis and Characterization of Duplex DNA Containing a New Base Pair: A Nondisruptive, Benzofused Pyrimidine Analog*, J. Org. Chem., 58:2232–2243, 1993.

* cited by examiner

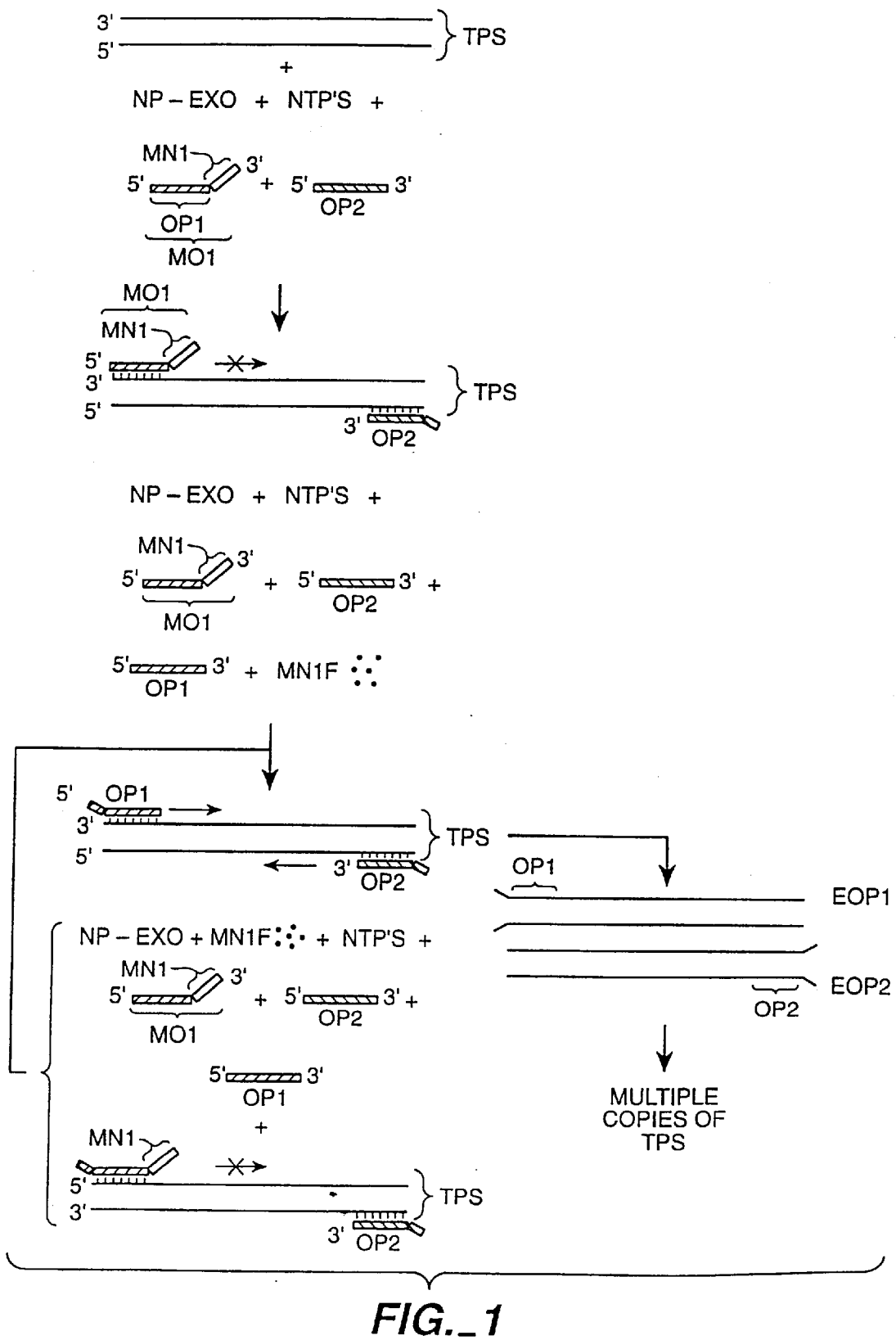
FIG._1

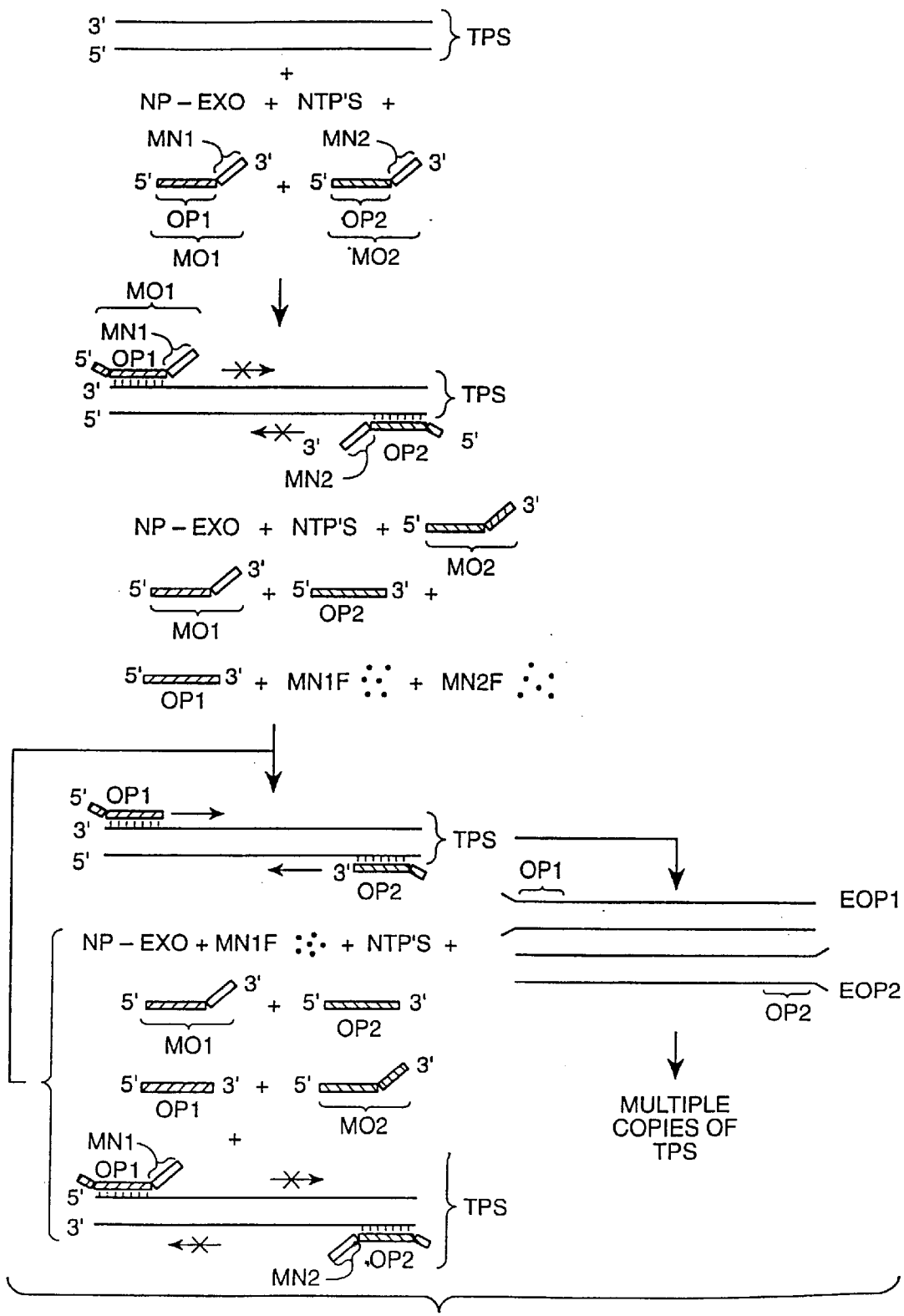
FIG._2

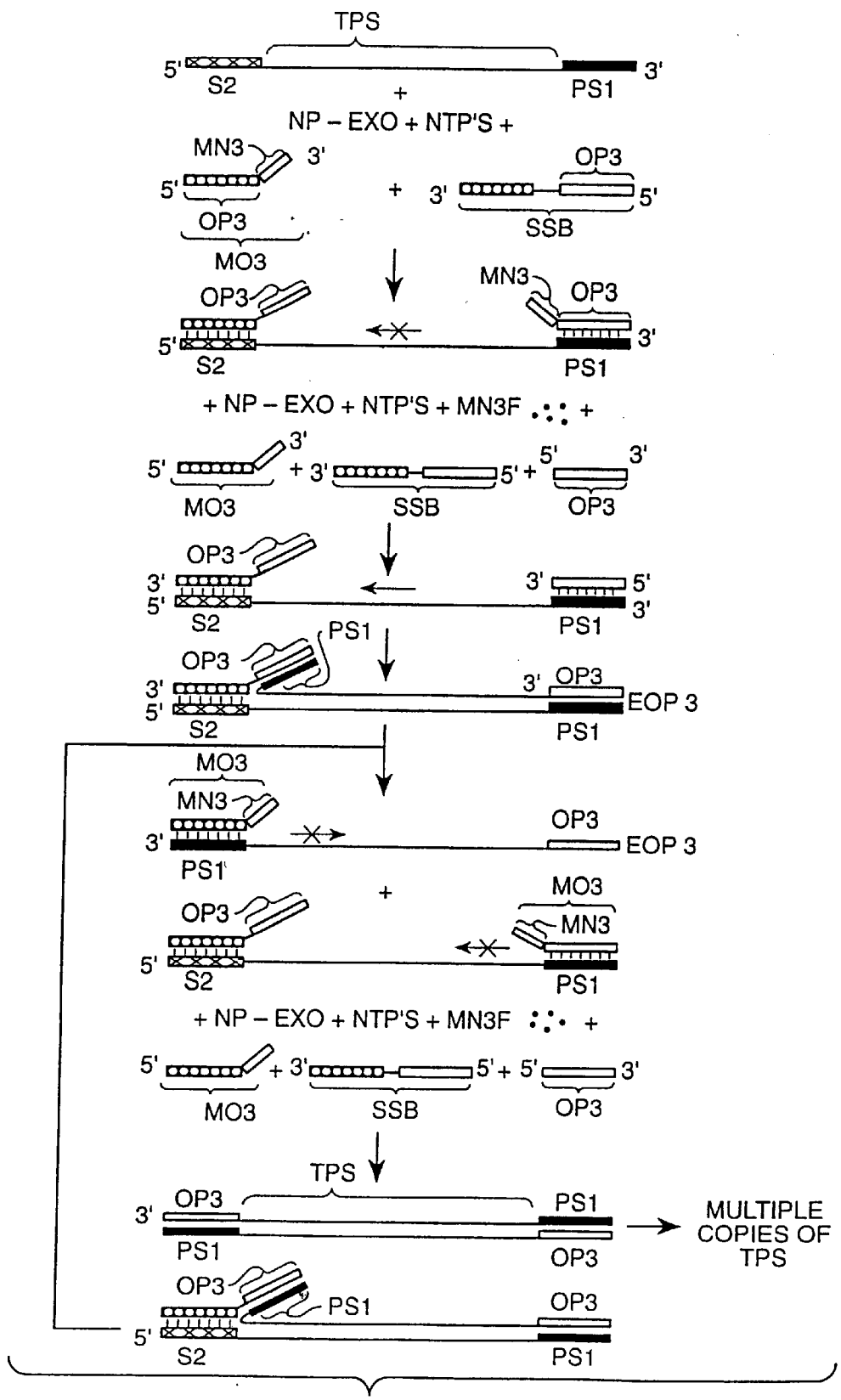
FIG._3

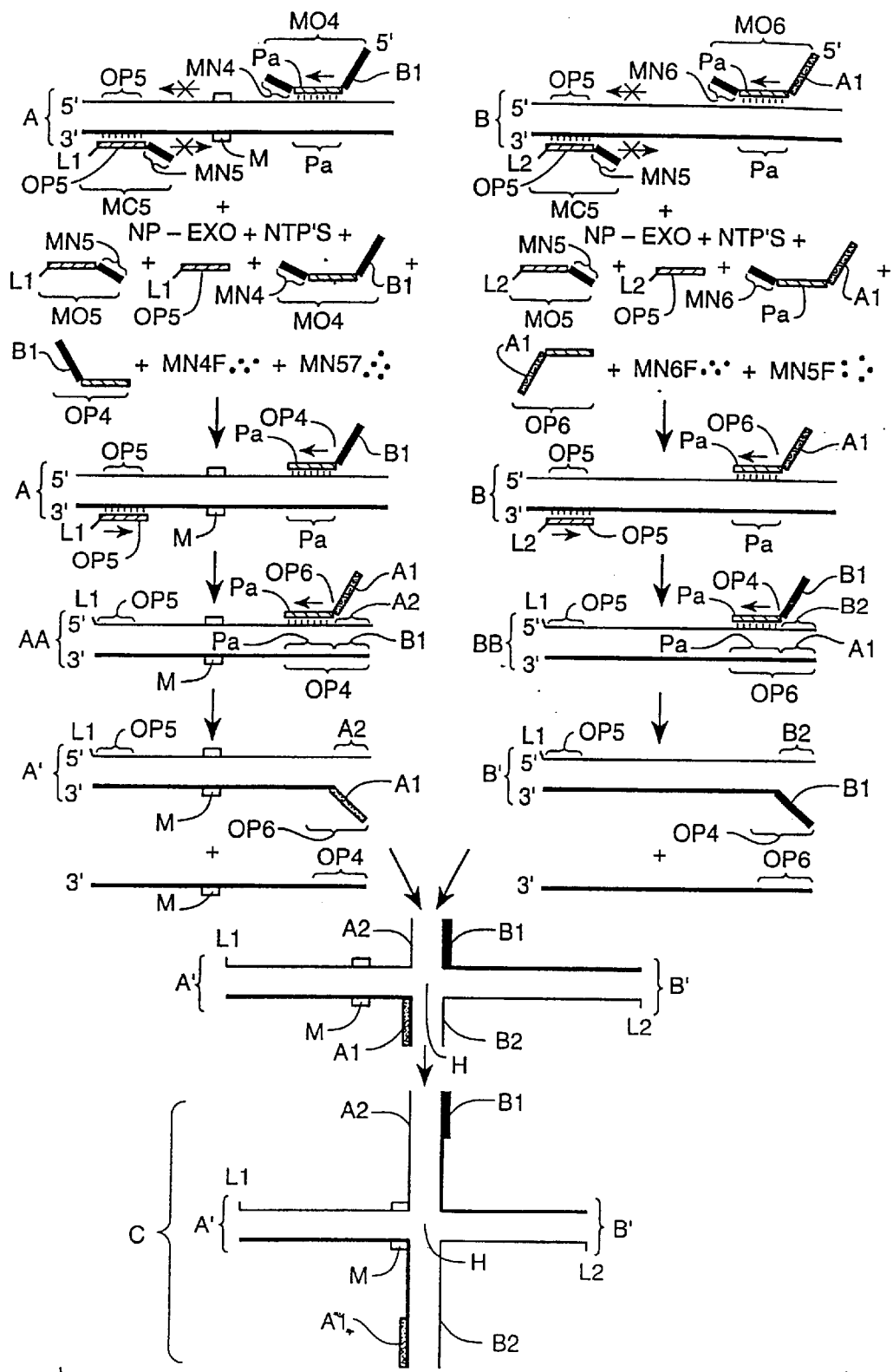
FIG._4

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

GCCTTTCAAA TTCAGATTGA GC    22

(2) INFORMATION FOR SEQ ID NO:2:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 23..24
        (D) OTHER INFORMATION: /note= "O-6-methyl deoxy G"

(xi) SEQUENCE DESCRIPTION: SEQ ID NO:2:

GCCTTTCAAA TTCAGATTGA GCNNG                                   25

(2) INFORMATION FOR SEQ ID NO:3:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 23..24
        (D) OTHER INFORMATION: /note= "O-4-methyl deoxy T"

(xi) SEQUENCE DESCRIPTION: SEQ ID NO:3:

GCCTTTCAAA TTCAGATTGA GCNNG                                   25

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 23..24
        (D) OTHER INFORMATION: /note= "etheno-deoxy A"

(xi) SEQUENCE DESCRIPTION: SEQ ID NO:4:

GCCTTTCAAA TTCAGATTGA GCNNG                                   25

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GACATTTACA GCAAATGCTT GC                                      22

(2) INFORMATION FOR SEQ ID NO:6:

(i) SEQUENCE CHARACTERISTICS:

(A) LENGTH: 25 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: -
            (B) LOCATION: 23..24
            (D) OTHER INFORMATION: /note= "etheno-deoxyA"

(xi) SEQUENCE DESCRIPTION: SEQ ID NO:6:

GACATTTACA GCAAATGCTT GCNNG                                               25

(2) INFORMATION FOR SEQ ID NO:7:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:7:

CAACTGTGGT TAAAGCAATA GTGT                                                24

(2) INFORMATION FOR SEQ ID NO:8:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:8:

GCACAGATTC TGAGTAACCA TAAT                                                24

(2) INFORMATION FOR SEQ ID NO:9:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:9:

ACCATGCTCG AGATTACGAG GACATTTACA GCAAATGCTT GC                            42

(2) INFORMATION FOR SEQ ID NO:10:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:10:

GATCCTAGGC CTCACGTATT GACATTTACA GCAAATGCTT GC                            42

(2) INFORMATION FOR SEQ ID NO:11:

```
        (i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: -
            (B) LOCATION: 43..44
            (D) OTHER INFORMATION: /note= "etheno-dA"

(xi) SEQUENCE DESCRIPTION: SEQ ID NO:11:

ACCATGCTCG AGATTACGAG GACATTTACA GCAAATGCTT GCNNG                     45

(2) INFORMATION FOR SEQ ID NO:12:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: -
            (B) LOCATION: 43..44
            (D) OTHER INFORMATION: /note= "etheno-dA"

(xi) SEQUENCE DESCRIPTION: SEQ ID NO:12:

GATCCTAGGC CTCACGTATT GACATTTACA GCAAATGCTT GCNNG                     45
```

METHOD FOR POLYNUCLEOTIDE AMPLIFICATION

This application claims priority to U.S. Provisional Patent Application No. 60/033,137 filed Dec. 20, 1996

BACKGROUND OF THE INVENTION

1 Field of the Invention

Significant morbidity and mortality are associated with infectious diseases. More rapid and accurate diagnostic methods are required for better monitoring and treatment of disease. Molecular methods using DNA probes, nucleic acid hybridizations and in vitro amplification techniques are promising methods offering advantages to conventional methods used for patient diagnoses.

A method for the enzymatic amplification of specific segments of DNA known as the polymerase chain reaction (PCR) method has been described. This in vitro amplification procedure is based on repeated cycles of denaturation, oligonucleotide primer annealing, and primer extension by thermophilic polymerase, resulting in the exponential increase in copies of the region flanked by the primers. The different PCR primers, which anneal to opposite strands of the DNA, are positioned so that the polymerase catalyzed extension product of one primer can serve as a template strand for the other, leading to the accumulation of a discrete fragment whose length is defined by the distance between the 5' ends of the oligonucleotide primers.

Another method has also been described for amplifying nucleic acid sequences. This method is referred to as single primer amplification. The method provides for the amplification of a target sequence that possesses a stem-loop or inverted repeat structure where the target sequence is flanked by relatively short complementary sequences. Various methods for creating such a target sequence in relation to the presence of a polynucleotide analyte to be detected have also been described.

The amplification methods described above require that samples suspected of having a specific nucleotide sequence be heated at about 95° C. and then be repetitively thermally cycled between one or two lower temperatures and about 95° C. The higher temperatures denature duplexes and the lower temperatures permit hybridization of the primer and chain extension.

The above methods are extremely powerful techniques for high sensitivity detection of target DNA molecules present in very small amounts. The correlation between the number of original target DNA molecules and the number of specifically amplified products is influenced by a number of variables. Minor variations in buffer or temperature conditions can greatly influence reaction-to-reaction amplification efficiencies. Further, clinical samples of DNA targets can contain inhibitory factors that can suppress enzymatic amplification. In addition, such clinical samples also contain irrelevant DNA, which can be present in very large amounts relative to the target DNA molecules.

The above amplification methods suffer from interference caused by random partial hybridization of primers used in such amplification to irrelevant DNA, i.e., DNA that is not target DNA and to which the primers bind non-specifically or non-selectively. A competition between target DNA and irrelevant DNA for the enzyme and the primer thus is created. As a result the efficiency of the amplification of the target DNA molecules is decreased. At best this leads to difficulty in distinguishing amplified target DNA from amplified irrelevant DNA. The amplification of irrelevant DNA to any substantial degree can interfere with specific amplification of target DNA to prevent detection of the target DNA completely.

One approach for this problem is to avoid chain extension of low temperature non-specifically hybridized primers by heating the reaction mixture to 95° C. prior to adding a critical reagent such as a polymerase enzyme or magnesium that is required to activate the polymerase. This can be accomplished by using a wax layer to separate the various reaction components until a high temperature is reached. Alternatively, an inhibitory antibody against the polymerase can be added at low temperature. The antibody denatures at elevated temperature and allows the enzyme to become reactivated. Another approach involves the use of AmpliTaq Gold® enzyme as the polymerase in PCR reactions.

Another method involving chain extension of an oligonucleotide primer is a method for the detection of differences in nucleic acids described in U.S. Patent Application Serial No. 60/009,289, the disclosure of which is incorporated herein by reference. Briefly, the branch migration method detects a difference between two related nucleic acid sequences. In the method, if there is a difference between the two related nucleic acid sequences, a stable quadramolecular complex is formed comprising both of the nucleic acid sequences in double stranded form. Usually, the complex comprises a Holliday junction. Both members of at least one pair of non-complementary strands within the complex have labels. The association of the labels as part of the complex is determined as an indication of the presence of the difference between the two related sequences. The method may be employed for detecting the presence of a mutation in a target nucleic acid sequence or for detecting the presence of a target nucleic acid sequence.

In the above method for the detection of differences between two related DNA sequences, non-specific priming can be a problem for mutation detection by inhibition of DNA branch migration. All amplification products incorporate the "tail" sequences of the reverse primers and hence are able to participate in the formation of four-stranded DNA complexes with both specific PCR products and with each other. Since the sequences on both sides of the junction are completely different from each other, such complexes never undergo strand separation by branch migration and thus generate non-specific signal. One approach to alleviate this problem is to use a two-step PCR procedure or nested PCR. It is highly desirable, however, to perform the above method using a single PCR reaction with just one set of primers.

A method for avoiding the above problems that is inexpensive and more controllable than the approaches mentioned above is desirable.

2. Description of the Related Art

A simplified hot start PCR using AmpliTaq Gold® enzyme is discussed by Birch, et al., *Nature* (1996) 381:445–446.

A hot start procedure using wax beads is disclosed by Chou, et al., *Nucleic Acids Research* (1992) 20:1717–1723.

W. B. Barnes discusses PCR amplification of up to 35-kb DNA with high fidelity and high yield from λ-bacteriophage templates in *Proc. Nat. Acad. Sci. USA* (1994) 91:2216–2220.

A process for amplifying, detecting and/or cloning nucleic acid sequences is disclosed in U.S. Pat. Nos. 4,683,195, 4,683,202, 4,800,159, 4,965,188 and 5,008,182. Sequence polymerization by polymerase chain reaction is described by Saiki, et al., (1986) *Science,* 230: 1350–1354. Primer-directed enzymatic amplification of DNA with a thermostable DNA polymerase is described by Saiki, et al., *Science* (1988) 239:487.

U.S. Pat. No. 5,508,178 (Rose, et al.) describes nucleic acid amplification using a single polynucleotide primer. U.S. patent application Ser. No. 08/140,349 filed Oct. 20, 1993 (Laney, et al.), describes methods of introducing defined sequences at the 3'-end of polynucleotides. The disclosures of these references are incorporated herein by reference.

Amplification of nucleic acid sequences using oligonucleotides of random sequence as primers is described in U.S. Pat. No. 5,043,272 (Hartley).

Nickel, et al., *J. Biol. Chem.* (1992) 267:848–854 describes interactions of azidothymidine triphosphate with the cellular DNA polymerases α, δ and ε and with DNA primase.

EP 0 439 182 (Backman, et al.) discusses methods of amplifying target nucleic acids applicable to both polymerase and ligase chain reactions.

SUMMARY OF THE INVENTION

In its broadest aspect the present invention relates to a method for controlling the concentration of an oligonucleotide primer in a reaction medium for conducting a reaction in which the oligonucleotide primer is extended along a polynucleotide template in the presence of reagents for carrying out such extension, e.g., a nucleotide polymerase and nucleoside triphosphates. A reaction medium is provided that comprises a modified oligonucleotide together with reactants for extending the oligonucleotide primer along the polynucleotide template. The modified oligonucleotide has a degradable 3'-end that is substantially incapable of being extended along the polynucleotide template. Degradation of the 3'-end of the modified oligonucleotide results in the formation of the oligonucleotide primer. The reaction medium is subjected to controlled conditions for degrading the 3'-end of the modified oligonucleotide thereby forming the oligonucleotide primer in a controlled manner for its extension along the polynucleotide template.

Another aspect of the present invention is a method for selectively extending an oligonucleotide primer along a specific target polynucleotide sequence in a mixture of polynucleotides. The method comprises providing in combination a mixture of polynucleotides and a modified oligonucleotide having a 3'-end that is not extendable along any polynucleotide and extending degraded modified oligonucleotide along the specific target polynucleotide sequence by controlling the degradation of the 3'-end of the modified oligonucleotide to give degraded modified oligonucleotide, which serves as an oligonucleotide primer in a chain extension reaction. In this way extension of the oligonucleotide primer along polynucleotides other than the specific target polynucleotide sequence is substantially reduced or avoided.

In another aspect the present invention provides an improvement in a method for amplifying a target polynucleotide sequence. The method comprises combining the target polynucleotide sequence with reagents for amplifying the target polynucleotide sequence and subjecting the combination to conditions wherein the target polynucleotide sequence is amplified. The reagents comprise a modified oligonucleotide and a polymerase. The improvement comprises the modified oligonucleotide having a portion that hybridizes to the target polynucleotide sequence except for the 3'-end thereof, which has at least one nucleotide analog that is incapable of hybridizing to a polynucleotide.

Another embodiment of the present invention is a method for amplifying a target polynucleotide sequence. A combination is provided that comprises the target polynucleotide sequence and reagents for conducting an amplification of the target polynucleotide sequence. The reagents comprise a polymerase, nucleoside triphosphates and a modified oligonucleotide, which comprises at least one nucleotide analog at the 3'-end thereof. The nucleotide analog is substantially non-hybridizable to any polynucleotide sequence and is also removable by a 3' to 5' exonuclease at a rate that is slower than for a natural nucleotide. The combination is subjected to conditions for amplifying the target polynucleotide sequence wherein the nucleotide analog is removed from the modified oligonucleotide. Extension of the oligonucleotide primer along the target polynucleotide sequence occurs to produce an extended oligonucleotide primer.

Another aspect of the present invention is a method for amplifying a target polynucleotide sequence in which the target polynucleotide sequence is combined with reagents for amplifying the target polynucleotide sequence and the combination is subjected to conditions to amplify the target polynucleotide sequence. The reagents comprise an oligonucleotide primer and a polymerase. The improvement comprises using a modified oligonucleotide having a portion that hybridizes to the target polynucleotide sequence except for the 3'-end thereof. The 3'-end is degradable at a rate of degradation that is slower for the modified oligonucleotide than for a corresponding oligonucleotide that does contain a modified nucleotide.

Another aspect of the present invention is an improvement in a method for forming multiple copies of a target polynucleotide sequence. A first oligonucleotide primer ("first primer") is hybridized to the 3'-end of the target sequence. The first primer is extended along at least the target sequence in the presence of a polymerase. The first primer is capable of hybridizing to, and being extended along extended first primer or an extended second oligonucleotide primer ("second primer") that is different from the first primer. The extended second primer results from the extension of a second primer capable of hybridizing to and extending along a polynucleotide that is complementary (complementary polynucleotide) to the target sequence. Extended first primer is dissociated from the target sequence. The first or second primer is hybridized to the 3'-end of the extended first primer. The first or second primer is extended along the extended first primer and extended first primer or extended second primer is dissociated from extended first primer. The first primer is hybridized to the 3'-end of the extended first or second primer. Steps (e)–(g) are repeated. The improvement comprises using a modified oligonucleotide in place of the first oligonucleotide primer. The modified oligonucleotide has a portion that hybridizes to the target polynucleotide sequence except for the 3'-end thereof, which 3'-end has at least one nucleotide analog that is incapable of hybridizing to a polynucleotide.

Another embodiment of the present invention is a kit comprising in packaged combination (a) a modified oligonucleotide comprising at least one nucleotide analog at the 3'-end thereof, the nucleotide analog being substantially non-hybridizable to any normal nucleotide in a polynucleotide sequence, and (c) a 3' to 5' exonuclease. In one embodiment the nucleotide analog is removable by a 3' to 5' exonuclease at a rate that is slower than for a natural nucleotide, (b) nucleoside triphosphates

BRIEF DESCRIPTION OF THE DRAWINGS

FIG. 1 is a schematic diagram depicting an embodiment in accordance with the present invention.

FIG. 2 is a schematic diagram depicting an alternate embodiment in accordance with the present invention.

FIG. 3 is a schematic diagram depicting an alternate embodiment in accordance with the present invention.

FIG. 4 is a schematic diagram depicting an alternate embodiment in accordance with the present invention.

DESCRIPTION OF THE SPECIFIC EMBODIMENTS

In the present invention an amplification of a target polynucleotide sequence is conducted using a modified oligonucleotide having one or more nucleotides at the 3'-end that are modified to render them unnatural resulting in inhibition of their ability to hybridize to natural nucleotides in DNA or in inhibition of chain extension by other means. The modified oligonucleotides used are not extendable on either the desired complementary target polynucleotide sequence or on irrelevant DNA, to which the primer may non-specifically bind. When all of the amplification reagents are mixed with the sample, extension of the primer along any polynucleotide present in the mixture is inhibited because of the presence of at least one unnatural nucleotide at the 3'-end. Modifications are chosen so as to obtain modified nucleotides that are relatively resistant to 3'-exonuclease activity but undergo slow degradation to remove the modified nucleotides as the temperature is increased. Upon removal of the modified nucleotides, the degraded modified oligonucleotide is an oligonucleotide primer that undergoes chain extension along the target polynucleotide sequence. The background products resulting from amplification of irrelevant DNA are greatly decreased because hybridization leading to chain extension only takes place at an elevated temperature where binding is relatively selective.

In essence, the control of the amplification in accordance with the present invention is achieved as a result of controlling the in situ concentration of the oligonucleotide primer. This is accomplished by utilizing a modified oligonucleotide having a degradable 3'-end that is substantially incapable of being extended along, or inefficiently extendable along, the target polynucleotide sequence or polynucleotide template. Degradation of the 3'-end of the modified oligonucleotide results in the formation of the oligonucleotide primer. The reaction medium is subjected to controlled conditions for degrading the 3'-end of the modified oligonucleotide thereby forming the oligonucleotide primer in a controlled manner for its extension along the polynucleotide template.

The present method has application to a number of procedures where amplification of a target polynucleotide sequence is carried out using thermal cycling. The use of the present method eliminates the use of nested primers or other means that were previously required to provide sufficiently low background for an amplification method to provide a meaningful result.

Before proceeding further with a description of the specific embodiments of the present invention, a number of terms will be defined.

Chain extension of an oligonucleotide—extension of an oligonucleotide along a polynucleotide template (chain of nucleotides) to produce a chain extension product that is the complement of the polynucleotide template. In the context of an amplification chain extension usually involves temperature cycling, i.e., elevating the temperature of the reaction mixture to cause hybridized polynucleotide sequences to denature, cooling the reaction mixture to permit binding of an oligonucleotide primer to its respective target polynucleotide sequence and subsequent extension along the target polynucleotide sequence, elevating the temperature of the reaction medium to cause hybridized polynucleotide sequences to denature, and repeating the above. In general, in primer extension amplification primers hybridize to, and are extended along (chain extended along), at least the target sequence within the target polynucleotide and, thus, the target sequence acts as a template. The extended primers are "chain extension products." Reagents for carrying out a chain extension of an oligonucleotide primer along a polynucleotide template include a nucleotide polymerase and nucleoside triphosphates.

One important method utilizing chain extension of an oligonucleotide primer is that for the amplification of nucleic acids or polynucleotides, such as a target polynucleotide sequence. Such methods generally result in the formation of one or more copies of a nucleic acid or polynucleotide molecule or in the formation of one or more copies of the complement of a nucleic acid or polynucleotide molecule, usually a target polynucleotide sequence, present in a medium.

One such method for the enzymatic amplification of specific double stranded sequences of DNA is known as the polymerase chain reaction (PCR), as described above. This in vitro amplification procedure is based on repeated cycles of denaturation, annealing of at least two different oligonucleotide primers, and primer extension, i.e., "chain extension" of such primers, by thermophilic template dependent polynucleotide polymerase, resulting in the exponential increase in copies, i.e., "chain extension products of the above primers," of the target polynucleotide sequence flanked by the primers. The two different PCR primers, which anneal to opposite strands of the DNA, are positioned so that the polymerase catalyzed extension product of one primer can serve as a template strand for the other, leading to the accumulation of a discrete double stranded fragment whose length is defined by the distance between the 5' ends of the oligonucleotide primers.

Another method for amplification is mentioned above and involves amplification of a single stranded polynucleotide using a single polynucleotide primer. The single stranded polynucleotide that is to be amplified contains two non-contiguous sequences that are complementary to one another and, thus, are capable of hybridizing together to form a stem-loop structure. This single stranded polynucleotide may be already part of a target polynucleotide sequence or may be created as the result of the presence of a target polynucleotide sequence.

Another method involving chain extension of an oligonucleotide primer is a method for the detection of differences in nucleic acids described in U.S. Patent Application Serial No. 60/009,289, the disclosure of which is incorporated herein by reference above. Generally, in the method a medium suspected of containing two related nucleic acid sequences is treated to provide two partial duplexes each comprised of fully matched duplexes having at one end non-complementary end portions. The partial duplexes are related in that, except for the difference, one of the strands S1 of one of the partial duplexes is complementary to one of the strands S1' of the other of the partial duplexes and the other of the strands S2 of one of the partial duplexes is complementary to the other of the strands S2' of the other of the partial duplexes. The medium is subjected to conditions that permit the binding of S1 to S1' and S2 to S2', respectively. If the medium contains a difference between the related nucleic acid sequences, a stable complex is formed comprising strands S1, S1', S2 and S2'. A determination is made whether the stable complex is formed, the presence thereof indicating the presence of a difference between the related nucleic acid sequences.

Nucleotide—a base-sugar-phosphate combination that is the monomeric unit of nucleic acid polymers, i.e., DNA and RNA.

Natural nucleotide—a nucleotide generally found in nature; such natural nucleotides include bases such as adenine, uridine, cytidine, thymidine, guanidine and so forth.

Modified nucleotide—is the unit in a modified oligonucleotide that differs from a natural nucleotide by some modification. The modified nucleotide is unable to hybridize to any natural nucleotide and/or to be extended by a polymerase along a template. The nature of the modified nucleotide for purposes of the present invention is described in more detail below in the definition of modified oligonucleotide.

Nucleoside—is a base-sugar combination or a nucleotide lacking a phosphate moiety.

Target polynucleotide sequence—a sequence of nucleotides to be identified, usually existing within a portion (target polynucleotide) or all of a polynucleotide analyte, the identity of which is known to an extent sufficient to allow preparation of various primers and other molecules necessary for conducting an amplification of the target sequence contained within the target polynucleotide. In general, in primer extension amplification primers hybridize to, and are extended along (chain extended along), at least the target sequence within the target polynucleotide and, thus, the target sequence acts as a template. The extended primers are "chain extension products." The target sequence usually lies between two defined sequences but need not. In general, the primers hybridize with the defined sequences or with at least a portion of such target polynucleotide, usually at least a ten nucleotide segment at the 3'-end thereof and preferably at least 15, frequently 20 to 50, nucleotide segment thereof. The target polynucleotide sequence usually contains from about 30 to 5,000 or more nucleotides, preferably 50 to 1,000 nucleotides. The target polynucleotide is generally a fraction of a larger molecule or it may be substantially the entire molecule. The minimum number of nucleotides in the target polynucleotide sequence is selected to assure that the presence of target polynucleotide in a sample can be determined. Very roughly, the sequence length is usually greater than about 1.6 log L nucleotides where L is the number of base pairs in the genome of the biologic source of the sample. The maximum number of nucleotides in the target polynucleotide is normally governed by the length of the polynucleotide analyte and its tendency to be broken by shearing, or other processes during isolation and any procedures required to prepare the sample for assay and the efficiency of detection and/or amplification of the sequence.

Oligonucleotide—a polynucleotide, usually single stranded, usually a synthetic polynucleotide but may be a naturally occurring polynucleotide. The oligonucleotide(s) are usually comprised of a sequence of 5 to 150 or more nucleotides, preferably, 10 to 100 nucleotides, more preferably, 15 to 50 nucleotides in length.

Various well-known techniques can be employed for preparing oligonucleotides. Such sequences can be obtained by biological synthesis or by chemical synthesis. For short sequences (up to about 100 nucleotides) chemical synthesis is frequently more economical as compared to biological synthesis. For longer sequences standard replication methods employed in molecular biology can be used such as the use of M13 for single stranded DNA as described by J. Messing, *Methods Enzymol*(1983) 101: 20–78.

In addition to standard cloning techniques, in vitro enzymatic methods may be used such as polymerase catalyzed reactions. For preparation of RNA, T7 RNA polymerase and a suitable DNA template can be used. For DNA, polymerase chain reaction (PCR) and single primer amplification are convenient.

Other chemical methods of polynucleotide or oligonucleotide synthesis include phosphotriester and phosphodiester methods (Narang, et al., *Meth. Enzymol* (1979) 68: 90) and synthesis on a support (Beaucage, et al., *Tetrahedron* (1981) Letters 22: 1859–1862) as well as phosphoramidate technique, Caruthers, M. H., et al., "Methods in Enzymology," Vol. 154, pp. 287–314 (1988), and others described in "Synthesis and Applications of DNA and RNA," S. A. Narang, editor, Academic Press, New York, 1987, and the references contained therein.

End of an oligonucleotide—as used herein this phrase refers to nucleotides, including the terminal nucleotide, at either the 3'- or 5'-opposing sides of an oligonucleotide.

Terminus of an oligonucleotide—as used herein this term refers to the terminal nucleotide at either the 3'- or 5'-end of an oligonucleotide.

Oligonucleotide primer(s)—an oligonucleotide that is usually employed in a chain extension on a polynucleotide template such as in, for example, an amplification of a nucleic acid. The oligonucleotide primer is usually a synthetic deoxynucleotide that is single stranded, containing a sequence at its 3'-end that is capable of hybridizing with a defined sequence of the target polynucleotide. Normally, an oligonucleotide primer, and particularly its 3'-end, has preferably 70%, more preferably 90%, most preferably 100%, complementarity to the defined sequence. The number of nucleotides in the hybridizable sequence of a oligonucleotide primer, which hybridizes to a target polynucleotide sequence, should be such that stringency conditions used to hybridize the oligonucleotide primer will prevent excessive random non-specific hybridization. The number of nucleotides in the oligonucleotide primer will be the same as the defined sequence of the target polynucleotide to which it binds, namely, at least 12 nucleotides, preferably, at least 15 nucleotides, and generally from about 12 to 50, preferably, 15 to 30, nucleotides.

Modified oligonucleotide—an oligonucleotide that possess one or more nucleotides having a chemical modification ("modified nucleotide" sometimes referred to herein as a "nucleotide analog") at the 3'-end thereof as compared to an oligonucleotide having a natural or unmodified nucleotide at its 3'-end. For the purpose of defining the position of a modified nucleotide, 3'-end includes any of the last three ribophosphates at the 3'-terminus of the oligonucleotide, usually any of the last two ribonucleotides. The modified nucleotide is unable to hybridize to any substantial degree to any natural nucleotide and, thus, the modified oligonucleotide is unable to chain extend, i.e., not extendable, along a polynucleotide to which it is hybridized. Accordingly, chain extension does not occur to any substantial degree unless and until the modification or the modified nucleotide is removed. The modified nucleotide(s) render the 3'-end of the modified oligonucleotide substantially incapable of hybridizing with a target polynucleotide sequence. While it is desirable in the present invention that the 3'-end be incapable of hybridizing to the target polynucleotide sequence, a small degree of hybridization, e.g., 1 to 5%, may be tolerated consistent with the aim of the present invention, namely, to substantially reduce the amount of background products in an amplification of a target polynucleotide sequence. Such a degree of tolerated hybridization may result in inefficient extension of the modified oligonucleotide along the target polynucleotide sequence and in that sense the modified oligonucleotide may be inefficiently extendable.

The modification provides for controlled degradation of the 3'-end portion of the modified oligonucleotide when the modified oligonucleotide is not hybridized to a target polynucleotide sequence. Modified nucleotides for the modified oligonucleotide are selected that reduce the rate of degradation and subsequent chain extension of the modified oligonucleotide by at least 20%, preferably, by at least 50 to 98%, seldom greater than 99%, the modified oligonucleotide being capable of storage with a polymerase, target polynucleotide and nucleoside triphosphates preferably for at least 5 minutes, more preferably, at least 10 minutes, at room temperature without substantial chain extension. It is also desirable that the 3'-end of the modified oligonucleotide be degradable no more rapidly and preferably 2 to 100 times slower when the modified oligonucleotide is hybridized to a polynucleotide sequence relative to when it is not hybridized.

The modified oligonucleotide has at least one modified nucleotide, preferably a contiguous sequence of 2 to 5 modified nucleotides terminating at the 3'-end of the primer. The modified nucleotides are usually attached directly to a sequence ("priming sequence") of about 12 to 50 nucleotides, preferably, about 15 to 30 nucleotides that are hybridizable with the intended "priming site" of the target polynucleotide sequence, i.e., the site to which degraded modified oligonucleotide is to bind for chain extension. Accordingly, such sequence of nucleotides is at least 80%, preferably, 90%, more preferably, 100%, complementary to the intended priming site. The 5'-end of the priming sequence may have a sequence of nucleotides, including modified nucleotides, that are not hybridizable with, or not complementary to, the priming site of the target polynucleotide sequence.

Any modification that accomplishes the purposes of the present invention may be utilized. The modification should be one that is degradable under the conditions of the reaction in which the modified oligonucleotide is used. On the other hand, the modification should not degrade so fast that one cannot obtain the control of degradation necessary to achieve the benefits of the present invention. The type and extent of modification of the 3'-end of the modified oligonucleotide is generally determined empirically with the goal of achieving the above parameters for control of degradation of the 3'-end of the modified oligonucleotide. For example, in determining the type and extent of modification subject to degradation by a 3' to 5' exonuclease, one can utilize a system in which the modified oligonucleotide is employed to generate an oligonucleotide primer for use as a forward primer in a reaction system mimicking a PCR amplification. Briefly, the modified oligonucleotide is combined in an appropriate medium for conducting PCR, which contains buffer, magnesium and a 3' to 5' exonuclease but not a target polynucleotide sequence. The reaction medium is subjected to thermal cycling for a period of time. Then, the modified oligonucleotide is used a forward primer in a PCR amplification in which a target polynucleotide sequence is present in the reaction medium. The extent of delay of the accumulation of an amplicon (chain extended oligonucleotide primer) is determined. This approach is described in more detail in Example 1 below, which is by way of illustration and not limitation.

One example of a modified nucleotide in a modified oligonucleotide in accordance with the present invention is a nucleotide that is substantially incapable of hydrogen bonding.

In one embodiment the modified nucleotide is a natural nucleotide that has a 3'-hydroxyl group that has been modified such as by formation of an ester, amide, sulfate or glycoside and thus is not chain extendable. Preferably, such a modified nucleotide is heat or light labile and thus the modified nucleotide is removable as the temperature of the reaction medium is raised or the medium is irradiated as the case may be. In another approach such a modified nucleotide may be removed enzymatically. Other methods of removal of such a modified nucleotide will be suggested to those skilled in the art in view of the above disclosure. For example, where the modification is an ester, removal is achieved in accordance with the present invention by use of an enzyme that is a thermally stable esterase. Alternatively, where a glycoside of the 3'-hydroxyl group is employed, the glycosidic linkage is cleaved by a thermally stable glycosidase. For example, a β-galactosyl group can be attached to the 3'-end of a modified oligonucleotide and a thermally stable β-galactosidase can be used in the reaction medium.

In another embodiment, the modification is selected such that the modified nucleotide or nucleotides are removed by an enzyme having 3'-exonuclease activity when the modified oligonucleotide is not bound to a sequence to which it can hybridize. One factor in the selection of the modified nucleotides in this approach is the specificity of the polymerase used in an amplification. The particular modified oligonucleotide chosen is one having one or more modified nucleotides at its 3'-end, which are then subjected to degradation by heating with the enzyme having 3'-exonuclease activity to be used. The rate of degradation can be readily followed by gel electrophoresis. Preferably, the rate should be slower than degradation of an unmodified oligonucleotide that is similar to the modified oligonucleotide but does not possess the modified nucleotides.

Where the rate is particularly slow, it will usually be desirable to include one or more groups in the complementary portion of the modified oligonucleotide that inhibit further degradation. This can be done, for example, by including phosphorothioates between the 3'-end of the modified oligonucleotide and the penultimate nucleotide of the portion of the modified oligonucleotide that is complementary to the target polynucleotide sequence. Optionally, phosphorothioates may be introduced at other sites near the 3'-end as well. These modified oligonucleotides, when subjected to 3'-exo$^+$-polymerase catalyzed degradation in accordance with the present invention, will be resistant to degradation past the phosphorothioate groups.

Chemical modifications of a natural nucleotide to produce an unnatural or modified nucleotide are described hereinbelow by way of example and not limitation. Ethenoadenosine has an ethylene bridge between the 6-amino group and the ring nitrogen at position 1 that blocks any possible hydrogen bonding. Other modifications include alkylation at the 6-oxygen of guanine, the 4-oxygen of thymine, the ring nitrogens at the 5-position of the purines, or the 3-positions of the pyrimidines, or the removal of the 2-amino group of guanine or the 4-amino group of cytosine. Heterocyclic groups other than purines and pyrimidines can also be used. In that regard it is preferable to use derivatives that can be purchased in a form convenient for solid state synthesis of the modified oligonucleotide, usually as phosphorimidates. Other heterocycles include, for example, triazine, unsubstituted pyrimidine, pyridines, deazapurines, pyridopyrroles and the like. The particular structure of the modified nucleotide is not critical so long as the enzyme can remove it when it is not hybridized and so long as it does not support chain extension.

Another example, by way of illustration and not limitation, of a suitable modification is a nucleotide that is modified on the ribose. Ribonucleotides are candidates because oligonucleotides terminating in ribonucleotides cannot be extended by most polymerases. When ribonucleotides are employed, an enzyme must be included that can exolytically remove the ribonucleotide from the modified oligonucleotide when the modified oligonucleotide is not hybridized to a complementary strand and cannot readily remove the ribonucleotide when the primer is hybridized. Other examples of modification of the ribose include 3'-deoxy derivatives including those in which the 3'-hydroxy is replaced by a functionality other than hydrogen such as an azide group.

Many modified nucleotides and oligonucleotides containing such modified nucleotides are commercially available or known in the literature. For example, etheno-deoxy A, O-6-methyl deoxy G and O-4-methyl deoxy T are commercially available from Oligos Etc., Wilsonville, Oreg. Non-hydrogen bonding nucleosides are discussed by Moran, et al., in *Nucleic Acids Research* (1996) 24(11):2044–2052 and include 4-methlyindole β-nucleoside, α-naphthalene nucleoside, α-pyrene nucleoside, and the like. N3-(β-D-ribofuranoside derivatives such as 4-amino-1-(2'-deoxy-β-D-ribofuranosyl)-2(1 H)-pyridinone and oligonucleotides comprising such modified nucleotides are disclosed by Charczuk, et al., in *Helv. Chim. Acta* (1987) 70(3):717–725. Huang, et al., discuss arabinosylcytosine 5'-triphosphate and other modified nucleosides in *Cancer Res* (1991) 51:6110–6117. Solomon, et al., disclose C-linked deoxyribosides of 2-hydroxypyridine and 2-hydroxyquinoline in *Tetrahedron Letters* (1991) 32(28):3297–3300; see also Solomon, et al., *J. Org. Chem.* (1993) 58:2232–2243. Other modified nucleosides and modified oligonucleotides may be synthesized by employing well-known synthetic techniques.

The chemical modification can be introduced into the oligonucleotide to be modified by various well-known techniques as described above for the preparation of oligonucleotides in general. Both biological synthesis or chemical synthesis can be employed. In one approach phosphotriester and phosphodiester methods can be used (Narang, et al., *Meth. Enzymol* (1979) 68: 90) and synthesis on a support (Beaucage, et al., *Tetrahedron* (1981) Letters 22: 1859–1862) as well as phosphoramidate technique, Caruthers, M. H., et al., "Methods in Enzymology," Vol. 154, pp. 287–314 (1988), and others described in "Synthesis and Applications of DNA and RNA," S. A. Narang, editor, Academic Press, New York, 1987, and the references contained therein. Controlled pore glass having a modified nucleotide bound to the surface is available for solid phase DNA synthesis employing the phosphoramidate technique. Accordingly, both automated and manual synthesis can be carried out. Modified oligonucleotides containing more than one modified nucleotide can be prepared in a similar manner by adding a modified nucleotide that has a 3'-hydroxyl to which another modified nucleotide can be added and repeating this process.

In addition to standard cloning techniques, in vitro enzymatic methods may be used such as polymerase catalyzed reactions. For preparation of RNA, T7 RNA polymerase and a suitable DNA template can be used. For DNA, polymerase chain reaction (PCR) and single primer amplification are convenient.

In another approach the 3'-hydroxyl group of a natural nucleotide may be derivatized by adding a single modified nucleotide in solution phase.

Some of the references cited above disclosing modified nucleosides that can be used in the present invention also describe syntheses of oligonucleotides containing the modified nucleotides. See, for example, Solomon, et al., *J. Org. Chem.* (1993) 58:2232–2243 and Charczuk, et al., in *Helv. Chim. Acta* (1987) 70(3):717–725.

Phosphorothioate—a nucleotide monophosphate in which an oxygen of at least one phosphate has been replaced by sulfur. An oxygen of 1 to 5 phosphates may be replaced by sulfur, more preferably, the oxygen of 1 to 2 phosphates is replaced. The sulfur is frequently bound solely to phosphorus (phosphorothioate group), but can also be bound to a ribose carbon atom or carbon atom of a label. Thus, such modified oligonucleotides contain at least one, preferably 1 to 5, more preferably, 1 to 2, phosphorus-sulfur bonds. These sulfur-containing modified oligonucleotides can be prepared according to known techniques. See, for example, WO9008838, WO8911486, U.S. Pat. No. 4,910,300, EP318245, the relevant disclosures of which are incorporated herein by reference. Other methods of preparing a phosphorothioate containing polynucleotide are described by (a) Yau, et al., *Tetrahedron Lett.* (1990)31(14): 1953–1956; (b) Brill, et al., ibid. (1989) 30(48):6621–6624; (c) Caruthers, et al., *Nucleic Acids Symp. Ser.* (1989)21: 119–120; (d) Caruthers, et al., *Nucleosides Nucleotides* (1988)8(5–6): 1011–1014; (e) Brill, et al., *J. Am. Chem. Soc.* (1989)111(6): 2321–2322.

Nucleoside triphosphates—nucleosides having a 5'-triphosphate substituent. The nucleosides are pentose sugar derivatives of nitrogenous bases of either purine or pyrimidine derivation, covalently bonded to the 1'-carbon of the pentose sugar, which is usually a deoxyribose or a ribose. The purine bases include adenine(A), guanine(G), inosine, and derivatives and analogs thereof. The pyrimidine bases include cytosine (C), thymine (T), uracil (U), and derivatives and analogs thereof. Nucleoside triphosphates include deoxyribonucleoside triphosphates such as dATP, dCTP, dGTP and dTTP and ribonucleoside triphosphates such as rATP, rCTP, rGTP and rUTP. The term "nucleoside triphosphates" also includes derivatives and analogs thereof, which are exemplified by those derivatives that are recognized and polymerized in a similar manner to the underivitized nucleoside triphosphates. Examples of such derivatives or analogs, by way of illustration and not limitation, are those which are modified with a reporter group, biotinylated, amine modified, radiolabeled, alkylated, and the like and also include phosphorothioate, phosphite, ring atom modified derivatives, and the like. The reporter group can be a fluorescent group such as fluorescein, a chemiluminescent group such as luminol, a terbium chelator such as N-(hydroxyethyl) ethylenediaminetriacetic acid that is capable of detection by delayed fluorescence, and the like. The term "nucleoside triphosphate" includes the derivatives and analogs thereof.

Nucleotide polymerase—a catalyst, usually an enzyme, for forming an extension of an oligonucleotide along a DNA template where the extension is complementary to the template. The nucleotide polymerase is a template dependent polynucleotide polymerase and utilizes nucleoside triphosphates as building blocks for extending the 3'-end of a oligonucleotide to provide a sequence complementary with the single stranded portion of the polynucleotide to which the oligonucleotide is hybridized to form a duplex. Usually, the catalysts are enzymes, such as DNA polymerases.

3' to 5' exonuclease—for purposes of the present invention an enzyme is considered to be a 3' to 5' exonuclease, or to have 3' to 5' exonuclease activity, when, under the conditions of the reactions contemplated herein, it catalyzes the removal or cleavage of nucleotides from the 3'-end of a modified oligonucleotide when such modified oligonucleotide is not hybridized to a target polynucleotide sequence and may also act as a nucleotide polymerase (in the latter sense it may be considered as a polymerase comprising a 3' to 5' exonuclease). The enzyme cleaves nucleotides of the oligonucleotide primer at least up to and including the modified nucleotides. At such point the degraded modified oligonucleotide is extendable at its 3'-terminus and can act as an oligonucleotide primer when hybridized to the target polynucleotide sequence. The 3' to 5'-exonucleases useful in the present invention must be stable under the conditions used in the present method and are usually thermally stable nucleotide polymerases.

Such enzymes may be derived from any source such as cells, bacteria, such as E. coli, plants, animals, virus, thermophilic bacteria, and so forth wherein the polymerase may be modified chemically or through genetic engineering to provide for thermal stability and/or increased activity. Such enzymes include Pfu DNA polymerase (native and recombinant) from Stratagene, La Jolla, Calif., Ultma DNA polymerase from Perkin Elmer, Foster City, Calif., r Bst DNA polymerase from Epicentre Technologies, Madison, Wis., VENT DNA polymerase from New England Biolabs, Beverly, Mass., Tli DNA polymerase from Promega Corp., Madison, Wis., and Pwo DNA polymerase from Boehringer Mannheim, Indianapolis, Ind., and the like.

Polynucleotide analyte—a compound or composition to be measured in an assay; a polymeric nucleotide, which in the intact natural state can have about 20 to 500,000 or more nucleotides and in an isolated state can have about 30 to 50,000 or more nucleotides, usually about 100 to 20,000 nucleotides, more frequently 500 to 10,000 nucleotides. It is thus obvious that isolation of the analyte from the natural state often results in fragmentation. The polynucleotide analytes include nucleic acids from any source in purified or unpurified form including DNA (dsDNA and ssDNA) and RNA, including t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like. The polynucleotide analyte can be only a minor fraction of a complex mixture such as a biological sample. The analyte can be obtained from various biological materials by procedures well known in the art. Some examples of such biological materials by way of illustration and not limitation are disclosed in U.S. Pat. No. 5,508,178 (Rose, et al.), the relevant portions of which are incorporated herein by reference.

Wholly or partially sequentially—when reagents utilized in the present invention are combined other than concomitantly (simultaneously), one or more may be combined with one or more of the remaining reagents to form a subcombination. Each subcombination can then be subjected to one or more steps of the present method. Thus, each of the subcombinations can be incubated under conditions to achieve one or more of the desired results.

Hybridization (hybridizing) and binding—in the context of nucleotide sequences these terms are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is achieved by elevating the temperature, increasing the ratio of cosolvents, lowering the salt concentration, and the like.

Homologous or substantially identical—In general, two polynucleotide sequences that are identical or can each hybridize to the same polynucleotide sequence are homologous. The two sequences are homologous or substantially identical where the sequences each have at least 90%, preferably 100%, of the same or analogous base sequence where thymine (T) and uracil (U) are considered the same. Thus, the ribonucleotides A, U, C and G are taken as analogous to the deoxynucleotides dA, dT, dC, and dG, respectively. Homologous sequences can both be DNA or one can be DNA and the other RNA.

Complementary—Two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence.

Copy of a sequence—a sequence that is a direct identical copy of a single stranded polynucleotide sequence as differentiated from a sequence that is complementary to the sequence of such single stranded polynucleotide.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These may be members of an immunological pair such as antigen-antibody, or may be operator-repressor, nuclease-nucleotide, biotin-avidin, hormones-hormone receptors, nucleic acid duplexes, IgG-protein A, DNA-DNA, DNA-RNA, and the like.

Ligand—any compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, repressors, protection enzymes, protein A, complement component C1q, DNA binding proteins or ligands and the like.

Small organic molecule—a compound of molecular weight less than 1500, preferably 100 to 1000, more preferably 300 to 600 such as biotin, fluorescein, rhodamine and other dyes, tetracycline and other protein binding molecules, and haptens, etc. The small organic molecule can provide a means for attachment of a nucleotide sequence to a label or to a support.

Support or surface—a porous or non-porous water insoluble material. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of sbp members to a support or surface may be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970). The surface can have any one of a number of shapes, such as strip, rod, particle, including bead, and the like.

Label or reporter group or reporter molecule—a member of the signal producing system. Usually the label or reporter group or molecule is conjugated to or becomes bound to a polynucleotide probe or an oligonucleotide primer and is capable of being detected directly or, through a specific binding reaction, and can produce a detectable signal. Labels include a polynucleotide primer or specific polynucleotide sequence that can provide a template for amplification or ligation or act as a ligand such as for a repressor protein. Preferably, an oligonucleotide primer will have, or be capable of having, a label. In general, any label that is detectable can be used. The label can be isotopic or nonisotopic, usually non-isotopic, and can be a catalyst, such as an enzyme, a polynucleotide coding for a catalyst, promoter, dye, fluorescent molecule, chemiluminescer, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, and the like. The label is a member of a signal producing system and can generate a detectable signal either alone or together with other members of the signal producing system. The label can be bound directly to a nucleotide sequence or can become bound thereto by being bound to an sbp member complementary to an sbp member that is bound to a nucleotide sequence.

Signal producing system—The signal producing system may have one or more components, at least one component being the label or reporter group. The signal producing system generates a signal that relates to the presence or amount of target polynucleotide sequence or a polynucleotide analyte in a sample. The signal producing system includes all of the reagents required to produce a measurable signal. When the label is not conjugated to a nucleotide sequence, the label is normally bound to an sbp member complementary to an sbp member that is bound to or part of a nucleotide sequence. Other components of the signal producing system may be included in a developer solution and can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, by use of electromagnetic radiation, desirably by visual examination. The signal-producing system is described more fully in U.S. Pat. No. 5,508,178 (Rose, et al.), the relevant disclosure of which is incorporated herein by reference.

Ancillary materials—Various ancillary materials will frequently be employed in the methods and assays carried out in accordance with the present invention. For example, buffers will normally be present in the assay medium, as well as stabilizers for the assay medium and the assay components. Frequently, in addition to these additives, proteins may be included, such as albumins, organic solvents such as formamide, quaternary ammonium salts, polycations such as dextran sulfate, surfactants, particularly non-ionic surfactants, binding enhancers, e.g., polyalkylene glycols, or the like.

As mentioned above, one aspect of the present invention is a method for amplifying nucleic acids wherein a modified oligonucleotide having a portion that is complementary to the nucleic acid is employed having at its 3'-end a group that can be catalytically removed by an enzyme. The group is not capable of being extended upon by the polymerase used in an amplification and must not be removed as rapidly as a natural nucleotide in a corresponding oligonucletide.

In the method an oligonucleotide primer is controllably generated and selectively extended along a target polynucleotide sequence in a mixture of polynucleotides. The mixture is provided in combination with a modified oligonucleotide having a 3'-end that is not extendable along any polynucleotide sequence to which it might bind. Controlled generation of an oligonucleotide primer is achieved by controlling the degradation of the 3'-end of the modified oligonucleotide to produce degraded modified oligonucleotide or oligonucleotide primer. In this way, small amounts of oligonucleotide primer are generated in situ and the generated oligonucleotide primer selectively binds to, and is extended along, the target polynucleotide sequence. Again, this is achieved by controlling the degradation of the 3'-end of the modified oligonucleotide. Since small amounts of the oligonucletide primer are controllably generated and because of the binding specificity of the generated oligonucletide primer for the target polynucleotide sequence, binding of the oligonucleotide primer to irrelevant polynucleotides is substantially reduced. Accordingly, extension of oligonucleotide primer along any polynucleotides in the reaction mixture other than the target polynucleotide sequence is avoided. Controlled degradation of the modified oligonucleotide provides for production of oligonucleotide primer that is extendable. Controlled production of the oligonucleotide primer provides for hybridization of such primer selectively to a target polynucleotide sequence and not to irrelevant polynucleotides because the production of such extendable primer occurs slowly and, therefore, its concentration at any point in time is low enough to permit selective hybridization to target polynucleotide sequence. Control of degradation may also be accomplished by selection of the type of modification in the modified oligonucleotide and the amount of the agent that removes the modification such as exo$^+$ polymerase, and esterase or light.

One embodiment of the present invention is depicted in FIG. 1. In this embodiment an amplification of a target polynucleotide sequence (TPS) by PCR amplification is chosen by way of example and not limitation. TPS is combined in a suitable buffered aqueous medium with modified oligonucleotide MO1 and oligonucleotide primer OP2, which are capable of hybridizing to one or the other strands of the double stranded TPS. MO1 contains portion MN1 that cannot hybridize with TPS because MN1 contains at least one modified nucleotide that is capable of being slowly degraded by a 3' to 5' exonuclease. Accordingly, MO1, when hybridized to TPS, cannot be extended along TPS, nor along any irrelevant DNA to which it might hybridize. Also included in the medium are nucleoside triphosphates (NTP's) and a nucleotide polymerase having 3' to 5' exonuclease activity (NP-exo). The temperature of the medium is relatively low, for example, being about 25° C. to 45° C. The ability of the 3' to 5' exonuclease to degrade portion MN1 of MO1 to give OP1 is increased as the temperature of the reaction medium is increased. Accordingly, as the temperature is raised, duplexes are denatured and MO1 is degraded to remove the modified nucleotides MN1F. As the temperature is lowered to about 70° C. to 80° C. during the next cycle and in the presence of the nucleoside triphosphates and nucleotide polymerase, OP1 is extended along the strand of TPS to which it selectively hybridizes to produce extended OP1 (EOP1). At the elevated temperature binding of nucleotide sequences to one another is more selective so that OP1, which is present in a relatively low concentration, selectively binds to TPS and the amount that may be bound to irrelevant DNA is very substantially reduced. As a result background products are greatly decreased. OP2 is also extended along the strand of TPS to which it is hybridized to produce extended OP2 (EOP2). Thermal cycling results in the continued controlled formation of OP1 from MO1, which leads to the production of multiple copies of TPS. Control of the temperature thus results in preferential extension of OP1 along TPS due to the controlled degradation of the modified portion of MO1.

To enhance the effect achieved in PCR through application of the present invention, MO2 containing modified portion MN2 is used in place of the unmodified OP2. Referring to FIG. 2, TPS is combined in a suitable buffered aqueous medium with two different oligonucleotide primers, modified oligonucleotide primer MO1 and modified oligonucleotide primer MO2, which are respectively capable of hybridizing to one of the strands of the double stranded TPS. As with MO1 above, MO2 contains portion MN2 that cannot hybridize with TPS because MN2 contains at least one modified nucleotide that is capable of being slowly degraded by a 3' to 5' exonuclease. Accordingly, MO2 cannot be extended along TPS, nor along any irrelevant DNA to which it might hybridize. Also included in the medium are nucleoside triphosphates (NTP's) and a nucleotide polymerase having 3' to 5' exonuclease activity (NP-exo). The temperature of the medium is relatively low, for example, being about 20° C. to 45° C. The ability of the 3' to 5' exonuclease to degrade portion MN1 of MO1 and portion MN2 of MO2 is increased as the temperature of the reaction medium is increased. Accordingly, as the temperature is raised, duplexes are denatured, MO1 is degraded to remove the modified nucleotides MN1F and MO2 is degraded to remove modified nucleotides MN2F. As the temperature is lowered to about 70° C. to 80° C. during the next cycle and in the presence of the nucleoside triphosphates and nucleotide polymerase, OP1 is extended along the strand of TPS to which it is hybridized to produce extended OP1 (EOP1) and OP2 is also extended along the strand of TPS to which it is hybridized to produce extended OP2 (EOP2). As above in the embodiment of FIG. 1, continued thermal cycling thus leads to the production of multiple copies of TPS. Control of the temperature thus results in preferential extension of OP1 and OP2 along TPS due to the controlled degradation of the modified portion of MO1 and MO2.

In applying the present invention to PCR amplification of nucleic acids, generally the reaction medium is cycled between two to three temperatures. The general principle in the present invention is that hybridization of the oligonucleotide primer to the target polynucleotide sequence take place only at elevated temperature where binding is relatively selective. Thus, binding of the oligonucleotide primer to irrelevant polynucleotides is minimized. Normally, in conducting the methods the medium is cycled between two or three temperatures. The temperatures for the methods generally range from about 10 to 105° C., more usually from about 40 to 99° C., preferably 50 to 98° C. The exact temperatures can be varied depending on the salt concentration, pH, solvents used, length of and composition of the target polynucleotide sequence and the primer. Relatively low temperatures of from about 30 to 65° C. can be employed for the extension steps, while denaturation and hybridization can be carried out at a temperature of from about 50 to 105° C. As mentioned above the reaction medium is initially at about 20° C. to 45° C., preferably, about 25° C. to 35° C. Relatively low temperatures of from about 50° C. to 80° C., preferably, 50° C. to 60° C., are employed for the hybridization or annealing steps, while denaturation is carried out at a temperature of from about 80° C. to 100° C., preferably, 90° C. to 95° C., and extension is carried out at a temperature of from about 70° C. to 80° C., usually about 72° C. to 74° C.

The amplification is conducted for a time sufficient to achieve a desired number of copies. Generally, the time period for conducting the method is from about 10 seconds to 10 minutes per cycle and any number of cycles can be used from 1 to as high as 60 or more, usually 10 to 50, frequently, 20 to 45. As a matter of convenience it is usually desirable to minimize the time period and the number of cycles. In general, the time period for a given degree of amplification can be minimized, for example, by selecting concentrations of nucleoside triphosphates sufficient to saturate the polynucleotide polymerase, by increasing the concentrations of polynucleotide polymerase and polynucleotide primer, and by using a reaction container that provides for rapid thermal equilibration. Generally, the time period for conducting the amplification in the method of the invention is from about 5 to 200 minutes. As a matter of convenience, it will usually be desirable to minimize the time period.

In carrying out the methods in accordance with the present invention, including amplification, an aqueous medium is employed. Other polar cosolvents may also be employed, usually oxygenated organic solvents of from 1–6, more usually from 1–4, carbon atoms, including alcohols, ethers and the like. Usually these cosolvents, if used, are present in less than about 70 weight percent, more usually in less than about 30 weight percent.

The pH for the medium is usually in the range of about 4.5 to 9.5, more usually in the range of about 5.5–8.5, and preferably in the range of about 6–8. The pH and temperature are chosen and varied, as the case may be, so as to cause, either simultaneously or sequentially, dissociation of any internally hybridized sequences, hybridization of oligonucleotide primer with the target polynucleotide sequence, degradation of the 3'-end of the oligonucleotide primer hybridized to the target polynucleotide sequence, extension of the primer(s), and dissociation of the extended primer(s). In some instances, a compromise is made in optimizing the speed, efficiency, and specificity of these steps depending on whether it is desired to perform the above steps sequentially or simultaneously. Various buffers may be used to achieve the desired pH and maintain the pH during the determination. Illustrative buffers include borate, phosphate, carbonate, Tris, barbital and the like. The particular buffer employed is not critical to this invention but in individual methods one buffer may be preferred over another.

The concentration of the enzyme having 3' to 5' exonuclease activity is sufficient to realize the requisite level of degradation of the oligonucleotide primer containing the modified nucleotide(s). The concentration is usually about 0.1 to 10 units per one hundred microliter reaction volume, preferably, 1 to 5 units per one hundred microliter reaction volume. Where such enzyme also functions as a polymerase, the concentration of this polymerase will be chosen to be sufficient to accomplish chain extension. The concentration of the polymerase is usually determined empirically. Preferably, a concentration is used that is sufficient such that further increase in the concentration does not decrease the time for the amplification by over 5-fold, preferably 2-fold. The primary limiting factor generally is the cost of the reagent. Where the exonuclease activity of the enzyme is great enough to result in premature degradation of the modified oligonucleotide primer at low temperature, the corresponding enzyme lacking exonuclease activity may be included in the reaction medium to provide, in effect, a dilution of the exonuclease activity of the overall concentration of enzyme. For example, if the enzyme used is Pfu polymerase, Pfu exo$^-$ may be included in the reaction medium in place of a portion of the Pfu polymerase. The amount of enzyme lacking exonuclease activity used is generally determined empirically as the amount that achieves an insubstantial level of degradation of the modified oligonucleotide primer at low temperature.

The amount of the target polynucleotide sequence that is to be copied can be as low as one or two molecules in a sample but generally may vary from about $10^2$ to $10^{10}$, more usually from about $10^3$ to $10^8$ molecules in a sample preferably at least $10^{-21}$M in the sample and may be $10^{-10}$ to $10^{-19}$M, more usually $10^{-14}$ to $10^{-19}$M.

The amount of the modified oligonucleotide is governed by the amount of oligonucleotide primer needed for the particular amplification or other reaction to which the present invention is applied. The amount of oligonucleotide primer(s) will be at least as great as the number of copies desired and will usually be $1 \times 10^{-10}$ to $1 \times 10^{-6}$ moles per sample, where the sample is 1–1,000 $\mu$L. Usually, the primer(s) are present in at least 0.1 $\mu$M, preferably 0.5 $\mu$M, and more preferably at least about 1 $\mu$M. Preferably, the concentration of the oligonucleotide primer(s) is substantially in excess over, preferably at least $1 \times 10^{14}$ times greater than, the concentration of the target polynucleotide sequence.

The concentration of the deoxynucleoside triphosphates in the medium can vary widely; preferably, these reagents are present in an excess amount. The deoxynucleoside triphosphates are usually present at $10^{-6}$ to $10^{-2}$M, preferably $10^{-5}$ to $10^{-3}$M.

The order of combining of the various reagents to form the combination may vary. Generally, the target polynucleotide sequence is obtained from a sample containing such sequence or a polynucleotide analyte that has been treated to obtain such sequence. Generally, the target polynucleotide sequence is combined with a pre-prepared combination of deoxynucleoside triphosphates and polymerase. The oligonucleotide primer(s) may be included in the prepared combination or may be added subsequently. However, simultaneous addition of all of the above, as well as other step-wise or sequential orders of addition, may be employed.

The concentration and order of addition of reagents and conditions for the method are governed generally by the desire to maximize the number of copies of the extended primer(s) and the rate at which such copies are formed and the fidelity of replication. Generally, it is desirable to increase the number of copies of the extended primer by at least a factor of $10^2$, preferably a factor of $10^4$, more preferably $10^6$ or more.

In carrying out the method of the invention as applied to the detection of a polynucleotide analyte, the considerations as to media, pH, temperature, and times can be as described above.

While the concentrations of the various reagents are generally determined by the concentration range of interest of the polynucleotide analyte, the final concentration of many of the reagents is normally determined empirically to optimize the sensitivity of the assay over the range of interest. The concentration of the other reagents in an assay generally is determined following the same principles as set forth above. The primary consideration is that a sufficient number of copies of extended primer(s) be produced in relation to the polynucleotide analyte sequence so that such copies can be readily detected and provide an accurate determination of the target polynucleotide sequence.

The copies of extended primer(s) can be detected in numerous ways. For example, in the present method, molecules of the oligonucleotide primer can be labeled with a reporter molecule such as a ligand, a small organic molecule, a polynucleotide sequence, a protein, support, a member of an operator-repressor pair, intercalation dye and the like. Any standard method for specifically detecting nucleic acid sequences can be used. Gel electrophoresis for detecting chain extension may be employed.

One method for detecting nucleic acids is to employ nucleic acid probes. One method utilizing probes is described in U.S. Pat. No. 4,868,104, the disclosure of which is incorporated herein by reference.

Other assay formats and detection formats are disclosed in U.S. Pat. Nos. 5,508,178, 5,439,998 and U.S. patent application Ser. No. 07/776,538 filed Oct. 11, 1991, which have been incorporated herein by reference.

Examples of particular labels or reporter molecules and their detection can be found in U.S. Pat. No. 5,439,998, the relevant disclosure of which is incorporated herein by reference.

Detection of the signal will depend upon the nature of the signal producing system utilized. If the label or reporter group is an enzyme, additional members of the signal producing system would include enzyme substrates and so forth. The product of the enzyme reaction is preferably a luminescent product, or a fluorescent or non-fluorescent dye, any of which can be detected spectrophotometrically, or a product that can be detected by other spectrometric or electrometric means. If the label is a fluorescent molecule the medium can be irradiated and the fluorescence determined. Where the label is a radioactive group, the medium can be counted to determine the radioactive count.

The present method has application where the target polynucleotide sequence is DNA or RNA.

In one aspect of the invention one or more of the reagents, such as, for example, a modified oligonucleotide and/or an oligonucleotide primer, is labeled with a label (reporter molecule). The reporter molecule can be, for example, a detectable group or a binder such as biotin or a nucleotide sequence other than the sequence that hybridizes with the target sequences. The extended primer(s) can be detected by means of a reporter molecule covalently bonded to a probe. The probe has a nucleotide sequence that is homologous or complementary to a portion of the target nucleotide sequence other than those sequences to which the primers bind.

The present invention also has application to amplification using a single oligonucleotide primer as described in U.S. Pat. No. 5,508,178 and U.S. patent application Ser. No. 08/140,349 filed Oct. 20, 1993. This embodiment is depicted in FIG. 3. A polynucleotide comprises a target polynucleotide sequence TPS and includes a first sequence of nucleotides designated primer binding site PS1 and a second sequence of nucleotides designated S2. The polynucleotide is combined in a suitable buffered aqueous medium with a single modified oligonucleotide MO3, which contains a sequence of nucleotides OP3 that is capable of hybridizing to PS1. MO3 contains portion MN3 that cannot hybridize with TPS because MN3 contains at least one modified nucleotide that is capable of being slowly degraded by a 3' to 5' exonuclease. Accordingly, MO3 cannot be extended along TPS, nor along any irrelevant DNA to which it might hybridize. Also included in the medium are nucleoside triphosphates (NTP's), a strand switch blocker (SSB) oligonucleotide (in accordance with the method of U.S. patent application Ser. No. 08/140,349 filed Oct. 20, 1993, referred to above) and a nucleotide polymerase having 3' to 5' exonuclease activity (NP-exo). The temperature of the medium is relatively low, for example, being about 25 to 45° C. The ability of the 3' to 5' exonuclease to degrade portion MN3 of MO3 to give OP3 is increased as the temperature of the reaction medium is increased. Accordingly, as the temperature is raised, duplexes are denatured and MO3 is degraded to remove the modified nucleotides MN3F. As the temperature is lowered to about 70° C. to 80° C. during the next cycle and in the presence of the nucleoside triphosphates, the strand switch blocker SSB and nucleotide polymerase, OP3 is extended along TPS to the point at which OP3 encounters SSB. At this point OP3 extends along that portion of SSB that is not hybridized to TPS. As a result extended OP3 (EOP3) is formed that includes sequence OP3 and sequence PS1, which is complementary to OP3 as well as TPS. EOP3 is then amplified during the thermal cycling by the single primer OP3, produced in a controlled manner by the degradation of MO3 in accordance with the present invention. Molecules of EOP3 serve as templates for primer OP3. Continued thermal cycling leads to the production of multiple copies of TPS. Control of the temperature thus results in preferential extension of OP3 along TPS due to the controlled degradation of the modified portion of MO3.

The present invention also has application to a method for detecting differences in related nucleic acid sequences. The method involves chain extension of oligonucleotide primers and is described in U.S. patent application Ser. No. 60/009,289, the disclosure of which was incorporated herein by reference above. Briefly, a combination of reagents is formed in the same reaction medium. The combination comprises (i) a sample containing a target nucleic acid sequence suspected of having a mutation, (ii) a reference nucleic acid sequence, which may be added separately if it is not known to be present in the sample and which corresponds to the target nucleic acid lacking the mutation, which may be the wild type nucleic acid, (iii) a nucleotide polymerase, (iv) nucleoside triphosphates, and (v) three oligonucleotide primers where two sets of one of the primers each may be labeled with different labels. The medium is then subjected to multiple temperature cycles of heating and cooling to simultaneously achieve all of the amplification and chain extension reactions. Preferably, in this embodiment, each cycle includes heating the medium at 90° C. to 100° C. for 10 seconds to 3 minutes, cooling the medium to 60° C. to 70° C. for a period of 10 seconds to 3 minutes, and heating the medium at 70° C. to 75° C. for a period of 10 seconds to 3 minutes although different temperatures may be required depending on the lengths of the primer sequences. Following the above temperature cycling the medium is subjected to heating for a period of time sufficient to denature double stranded molecules, preferably, at 90° C. to 99° C. for 10 seconds to 2 minutes, and cooled to 40° C. to 80° C., preferably 60° C. to 70° C., and held at this temperature for at least one minute, preferably for 20 minutes to 2 hours.

Following cooling of the medium (see FIG. 4), all possible partial and complete duplexes are formed that can form from 1) single strands that have any combination of reference or mutant sequences and 5'-ends A2 and B2, and 2) single strands having any combination of reference or mutant sequences and 5'-ends A1 or B1 wherein the strands may further be labeled with either L1 or L2 when L1 and L2 are different. Among the partial duplexes that are formed are the tailed partial duplexes A' and B', which can bind to each other to form complex C, which does not dissociate into duplexes D and E when a mutation is present. A determination of the presence of such a complex is then made to establish the presence of a mutation in the target nucleic acid sequence.

Referring to FIG. 4, the above reactions that occur simultaneously are described in a step-wise manner. In this embodiment with application of the present invention, three modified oligonucleotides are employed and are designated MO4, MO5 and MO6, respectively. In the embodiment shown in FIG. 4, by way of illustration and not limitation, two sets of modified oligonucleotide MO5 are employed wherein one set is labeled with L1 and the other set is labeled with L2. A tailed target partial duplex A' is produced from target nucleic acid duplex A having mutation M and tailed reference partial duplex B' is produced from reference nucleic acid duplex B.

Referring to FIG. 4, target nucleic acid A and reference nucleic acid B are combined in a suitable buffered aqueous medium with the modified oligonucleotides, MO4, MO5-L1 and MO5-L2, and MO6. In accordance with the present invention MO4 contains portion MN4 that does not hybridize to its respective strand of A and MO5-L1 contains portion MN5 that does not hybridize to its respective strand of A. Likewise, MO6 contains portion MN6 that does not hybridize to its respective strand of B and MO5-L2 contains portion MN5 that does not hybridize to is respective strand of B. Each of the portions MN4, MN5 and MN6 contain at least one modified nucleotide that is capable of being slowly degraded by a 3' to 5' exonuclease. Accordingly, MO4, MO5 and MO6 cannot be extended along the respective strands of A or B, nor along any irrelevant DNA to which they might hybridize.

Also included in the medium are nucleoside triphosphates (NTP's) and a nucleotide polymerase having 3' to 5' exonuclease activity (NP-EXO). The temperature of the medium is relatively low, for example, being about 25 to 45° C. The ability of the 3' to 5' exonuclease to degrade portion MN4 of MO4, MN5 of MO5 and MN6 of MO6 is increased as the temperature of the reaction medium is increased. Accordingly, as the temperature is raised, duplexes are denatured, MO4 is degraded to remove the modified nucleotides MN4F, MO5 is degraded to remove the modified nucleotides MN5F and MO6 is degraded to remove modified nucleotides MN6F. As the temperature is lowered to about 70° C. to 80° C. during the next cycle and in the presence of the nucleoside triphosphates and nucleotide polymerase, OP4, OP5 and OP6 are extended along the respective strands of A or B to which each is respectively hybridized. At the elevated temperature binding of nucleotide sequences to one another is more selective so that OP4, OP5 and OP6, which are present in a relatively low concentration, selectively binds to their respective strands of A and B so that the level at which OP4, OP5 and OP6 may be bound to irrelevant DNA is substantially reduced. Thus, consistent with the present invention, background products are greatly decreased.

As depicted In FIG. 4, A is amplified by the polymerase chain reaction using primers OP4 and OP5 to produce an amplicon AA. Primer OP5 contains a label L1 and primer OP4 is comprised of a 3'-end portion Pa that can hybridize with the target sequence and 5'-end portion B1 that cannot hybridize with the target sequence. The amplification is carried out in the presence of a nucleotide polymerase and nucleoside triphosphates using temperature cycling. Amplicon AA has two strands, a labeled strand derived from primer OP5 and an unlabeled strand derived from primer OP4. The unlabeled strand has a 5'-end portion B1 of primer OP4 and the labeled strand has a corresponding 3'-end portion A2, which is the complement of B1. Referring again to FIG. 4, chain extension of primer OP6 along the labeled strand of amplicon AA occurs to produce tailed target partial duplex A'. Primer OP6 is comprised of a 3'-end portion Pa, which is identical to Pa of primer OP4 and which binds to the labeled strand of AA. OP6 has 5'-end portion A1 that is not complementary to amplicon AA. In the embodiment of FIG. 4, the important strand is the complementary strand of the labeled strand and not its copy. The complementary unlabeled strand of tailed target partial duplex A' has a 5'-end portion A1, which is not complementary to the 3'-end portion A2 of the labeled strand of A'.

Again referring to FIG. 4, reference nucleic acid sequence B is comprised of a sequence identical to A except for mutation M. Primer OP5 contains label L2 that is different than L1. Amplicon BB has two strands, a labeled strand derived from the extension of primer OP5-L2 and an unlabeled strand derived from the extension of primer OP6. The unlabeled strand has end portion A1 of primer OP6 and the labeled strand has corresponding end portion B2, which is the complement of A1.

Chain extension of primer OP4 along the labeled strand of amplicon BB produces tailed reference partial duplex B'. As mentioned above, primer OP4 is comprised of portion Pa, which binds to the labeled strand of BB and portion B1 that does not bind to amplicon BB. The extension product of primer OP4 has a 5'-end portion B1, which is not complementary to end portion B2 of the labeled strand of B'. As can be seen, A' and B' are related in that each of their labeled strands is complementary, except for mutation M, to the unlabeled strand of the other.

The strands of partial duplexes A' and B' bind and undergo branch migration under the reaction conditions, for example, a temperature of 30° C. to 75° C., preferably 60° C. to 70° C., for at least one minute, preferably, 20 to 40 minutes, wherein complex C is formed. Oligonucleotide tail A1 of A' hybridizes to corresponding oligonucleotide tail B2 of B' and, similarly, oligonucleotide tail A2 of A' is hybridizes to oligonucleotide tail B1 of B'. Branch migration within complex C continues under the above temperature conditions with separation of the complex into duplexes D and E unless a mutation M is present, whereupon branch migration and strand dissociation is inhibited. Complex C is then detected, the presence of which is directly related to the presence of mutation M.

In the embodiment depicted in FIG. 4, labels L1 and L2 are incorporated into the partial duplexes that comprise complex C and provide a means for detection of complex C This is by way of illustration and not limitation and other convenient methods for detecting complex C may be employed, such as the use of a receptor for the complex. In this approach there is required only one label, L1 or L2, which comprises an sbp member or a reporter molecule. A receptor for the sbp member and a receptor that can bind to complex C by virtue of a feature other than L1 or L2 can both bind to complex C and provide a means for detection.

The conditions for carrying out the detection of differences in nucleic acids wherein the present invention is utilized are similar to those for the amplification described above. In general, the medium is heated to a temperature of 90° C. to 100° C. for a period of 5 to 500 seconds and then cooled to 20° C. to 80° C. for a period of 5 to 2000 seconds followed by heating to 40° C. to 80° C. for a period of 5 to 2000 seconds. Preferably, the medium is subjected to heating at 90° C. to 100° C. for a period of 10 seconds to 3 minutes, cooling to 50° C. to 65° C. for a period of 10 seconds to 2 minutes and heating to 70° C. to 80° C. for a period of 30 seconds to 5 minutes.

As a matter of convenience, predetermined amounts of reagents employed in the present invention can be provided in a kit in packaged combination. A kit can comprise in packaged combination an oligonucleotide primer comprising at least one nucleotide analog at the 3'-end thereof, nucleotide triphosphates and a 3' to 5' exonuclease. The nucleotide analog of the oligonucleotide primer is substantially non-hybridizable to any normal nucleotide in a polynucleotide sequence. In one embodiment the nucleotide analog has a 3'-hydroxyl group. In another embodiment the nucleotide analog is a natural nucleotide having a chemical modification that is removable. Preferably, the nucleotide analog is removable by an enzyme having 3' to 5' exonuclease activity at a rate that is slower than for a natural nucleotide. In the event that a nucleotide polymerase is included in the kit and the nucleotide polymerase does not have 3' to 5' exonuclease activity, then the kit further comprises an enzyme having 3' to 5' exonuclease activity.

A kit for amplification of a target polynucleotide sequence comprises the above items and for conducting PCR would include in addition a second polynucleotide primer, where the primers are related in that a product of the extension of one along said target sequence serves as a template for the extension of the other.

In assaying for a polynucleotide analyte in a sample, a kit useful in the present method can comprise, in packaged combination with other reagents mentioned above, reagents for forming a target polynucleotide sequence from a polynucleotide analyte. Furthermore, the oligonucleotide primer can be labeled or can be provided with groups to render the sequence labeled or bound to a support. The kit can further include a labeled polynucleotide probe capable of binding to an amplified target polynucleotide sequence. The kit can further include members of a signal producing system and also various buffered media, some of which may contain one or more of the above reagents.

The relative amounts of the various reagents in the kits can be varied widely to provide for concentrations of the reagents which substantially optimize the reactions that need to occur during the present method and to further substantially optimize the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. Each reagent can be packaged in separate containers or some reagents can be combined in one container where cross-reactivity and shelf life permit. The kit can further include a written description of a method in accordance with the present invention as described above.

EXAMPLES

The invention is demonstrated further by the following illustrative examples. Temperatures are in degrees centigrade (°C.) and parts and percentages are by weight, unless otherwise indicated.

The following definitions and abbreviations are used herein:

Tris—Tris(hydroxymethyl)aminomethane-HCl (a 10×solution) from BioWhittaker, Walkersville, Md.
HPLC—high performance liquid chromatography.
DTT—dithiothreitol
BSA—bovine serum albumin from Gibco BRL, Gaithersburg Md.
bp—base pairs
wt(+)—wild type allele
mut(−)—mutant allele
Target sample—DNA sample to be tested for the presence of a mutation;
sec—seconds
hr—hours
min—minutes
Buffer A—10 mM Tris-HCl (pH8.3), 50 mM KCl, 4 mM MgCl$_2$, 200 µg/ml BSA
Buffer C—0.1M Tris, 0.3M NaCl, 25 mM EDTA, 0.1% BSA, 0.1% dextran T-500, a 1:320 dilution of mouse IgG (HBR-1 from Scantibodies Laboratory Inc., Los Angeles, Calif.), 0.05% Kathon (Rohm and Haas, Philadelphia, Pa.), and 0.01% gentamycin sulfate.
RLU—relative light units
nt—nucleotides
MAD—maleimidylaminodextran
Ab—antibody
Sav—streptavidin
MOPS—3-(N-morpholino)propane sulfonic acid
hr—hour
sulfo-SMCC—sulfosuccinimidyl 4-(N-maleimidomethyl) cyclohexane-1-carboxylate
NHS—N-hydroxysuccinimide
EDAC—1-ethyl-3-(3-dimethylaminopropyl)carbodiimide hydrochloride
DMSO—dimethylsulfoxide
MES—morpholinoethanesulfonate
rpm—rotations per min
EDTA—ethylenediaminetetraacetic acid
SATA—N-succinimidyl S-acetylthioacetate
BSA—bovine serum albumin from Sigma Chemical Company, St. Louis Mo.
eq—equivalents
bp—base pairs
A$_{280}$—absorbance at wavelength 280 nanometers
DexAl—dextran aldehyde
DPP—4,7-diphenylphenanthroline
Eu(TTA)$_3$—europium tri-3-(2-thienoyl)-1,1,1-trifluoroacetonate
L or l—liter
exo VII—exonuclease VII from *E.coli* (from Amersham Life Science) (USB).
DMF—dimethyl formamide
THF—tetrahydrofuran
MS—mass spectroscopy
NMR—nuclear magnetic resonance spectroscopy
TMSCl—tetramethylsilylchloride
ELISA—enzyme linked immunosorbent assay as described in "Enzyme-Immunoassay," Edward T. Maggio, CRC Press, Inc., Boca Raton, Fla. (1980)

Monoclonal antibodies were produced by standard hybrid cell technology. Briefly, the appropriated immunogen was injected into a host, usually a mouse or other suitable animal, and after a suitable period of time the spleen cells from the host were obtained. Alternatively, unsensitized cells from the host were isolated and directly sensitized with the immunogen in vitro. Hybrid cells were formed by fusing the above cells with an appropriate myeloma cell line and culturing the fused cells. The antibodies produced by the cultured hybrid cells were screened for their binding affinity to the particular antigen, dig-BSA conjugate. A number of screening techniques were employed such as, for example, ELISA screens. Selected fusions were then recloned.

Beads

Acc-Ab$_{Dig}$—Acceptor beads coupled (MAD) to the anti-Dig antibody (with 377 antibody molecules per bead) were prepared as follows:

Hydroxypropylaminodextran (1NH$_2$/7 glucose) was prepared by dissolving Dextran T-500 (Pharmacia, Uppsala, Sweden) (50 g) in 150 mL of H$_2$O in a 3-neck round-bottom flask equipped with mechanical stirrer and dropping funnel. To the above solution was added 18.8 g of Zn (BF$_4$)$_2$ and the temperature was brought to 87° C. with a hot water bath. Epichlorohydrin (350 mL) was added dropwise with stirring over about 30 min while the temperature was maintained at 87–88° C. The mixture was stirred for 4 hr while the temperature was maintained between 80° C. and 95° C., then the mixture was cooled to room temperature. Chlorodextran product was precipitated by pouring slowly into 3 L of methanol with vigorous stirring, recovered by filtration and dried overnight in a vacuum oven.

The chlorodextran product was dissolved in 200 mL of water and added to 2 L of concentrated aqueous ammonia (36%). This solution was stirred for 4 days at room temperature, then concentrated to about 190 mL on a rotary evaporator. The concentrate was divided into two equal batches, and each batch was precipitated by pouring slowly into 2 L of rapidly stirring methanol. The final product was recovered by filtration and dried under vacuum.

Hydroxypropylaminodextran (1NH$_2$/7 glucose), prepared above, was dissolved in 50 mM MOPS, pH 7.2, at 12.5 mg/mL. The solution was stirred for 8 hr at room temperature, stored under refrigeration and centrifuged for 45 min at 15,000 rpm in a Sorvall RC-5B centrifuge immediately before use to remove a trace of solid material. To 10 mL of this solution was added 23.1 mg of Sulfo-SMCC in 1 mL of water. This mixture was incubated for 1 hr at room temperature and used without further purification.

C-28 thioxene was prepared as follows:

To a solution of 4-bromoaniline (30 g, 174 mmol) in dry DMF (200 mL) was added 1-bromotetradecane (89.3 mL, 366 mmol) and N,N-diisopropylethylamine (62.2 mL, 357 mmol). The reaction solution was heated at 90° C. for 16 hr under argon before being cooled to room temperature. To this reaction solution was again added 1-bromotetradecane (45 mL, 184 mmol) and N,N-diisopropylethylamine (31 mL, 178 mmol) and the reaction mixture was heated at 90° C. for another 15 hr. After cooling, the reaction solution was concentrated in vacuo and the residue was diluted with $CH_2Cl_2$ (400 mL). The $CH_2Cl_2$ solution was washed with 1N aqueous NaOH (2×), $H_2O$, and brine, was dried over $Na_2SO_4$ and was concentrated in vacuo to yield a dark brown oil (about 110 g). Preparative column chromatography on silica gel by a Waters 500 Prep LC system eluting with hexane afforded a yellow oil that contained mainly the product (4-bromo-N,N-di-($C_{14}H_{29}$)-aniline) along with a minor component 1-bromotetradecane. The latter compound was removed from the mixture by vacuum distillation (bp 105–110° C., 0.6 mm) to leave 50.2 g (51%) of the product as a brown oil. To a mixture of magnesium turnings (9.60 g, 395 mmol) in dry THF (30 mL) under argon was added dropwise a solution of the above substituted aniline product (44.7 g, 79 mmol) in THF (250 mL). A few crystals of iodine were added to initiate the formation of the Grignard reagent. When the reaction mixture became warm and began to reflux, the addition rate was regulated to maintain a gentle reflux. After addition was complete, the mixture was heated at reflux for an additional hour. The cooled supernatant solution was transferred via cannula to an addition funnel and added dropwise (over 2.5 hr) to a solution of phenylglyoxal (11.7 g, 87 mmol) in THF (300 mL) at $-30°$ C. under argon. The reaction mixture was gradually warmed to 0° C. over 1 hr an stirred for another 30 min. The resulting mixture was poured into a mixture of ice water (800 mL) and ethyl acetate (250 mL). The organic phase was separated and the aqueous phase was extracted with ethyl acetate (3×). The combined organic phases were washed with $H_2O$ (2×), brine and was dried over $MgSO_4$. Evaporation of the solvent gave 48.8 g of the crude product as a dark green oily liquid. Flash column chromatography of this liquid (gradient elution with hexane, 1.5:98.5, 3:97, 5:95 ethyl acetate:hexane) afforded 24.7 g (50%) of the benzoin product (MS ($C_{42}H_{69}NO_2$): $[M-H]^+$ 618.6, $^1H$ NMR (250 MHz, $CDCl_3$) was consistent with the expected benzoin product. To a solution of the benzoin product from above (24.7 g, 40 mmol) in dry toluene (500 mL) was added sequentially 2-mercaptoethanol (25 g, 320 mmol) and TMSCl (100 mL, 788 mmol). The reaction solution was heated at reflux for 23 hr under argon before being cooled to room temperature. To this was added additional TMSCl (50 mL, 394 mmol); and the reaction solution was heated at reflux for another 3 hr. The resulting solution was cooled, was made basic with cold 2.5N aqueous NaOH and was extracted with $CH_2Cl_2$ (3×). The combined organic layers were washed with saturated aqueous $NaHCO_3$ (2×) and brine, was dried over $Na_2SO_4$ and was concentrated in vacuo to give a brown oily liquid. Preparative column chromatography on silica gel by using a Waters 500 Prep LC system (gradient elution with hexane, 1:99, 2:98 ethyl acetate:hexane) provided 15.5 g (60%) of the C-28 thioxene as an orange-yellow oil (MS ($C_{44}H_{71}NOS$): $[M-H]^+$ 661.6, $^1H$ NMR (250 MHz, $CDCl_3$) was consistent with the expected C-28 thioxene product 2-(4-(N,N-di-($C_{14}H_{29}$)-anilino)-3-phenyl thioxene.

Carboxyl acceptor beads were prepared as follows:

The starting beads were carboxylate modified latex purchased from Seradyn Particle Technology, Indianapolis, Ind. The beads contained $Eu(TTA)_3DPP$ prepared as follows: $DPP/Eu(TTA)_3$ was prepared by combining 8.69 g of $Eu(TTA)_3 \cdot 3H_2O$ (10 mmoles, Kodak Chemical Company, Rochester N.Y.) and 1.8 g of 1,10-phenanthroline (10 mmoles, Aldrich) in 50 ml of dry toluene and heating to 95° C. in an oil bath for one 1 hour. Toluene was removed under reduced pressure. The ash colored solid was crystallized from 10 ml of toluene to yield 10 grams of $DPP/Eu(TTA)_3$. Absorption spectrum: 270 nm (20,000), 340 nm (60,000) (Toluene) 1.R(KBr): $Cm^{-1}$: 3440(s), 1600(s), 1540(s), 1400 (s), 1300(s). Four mL of 20% suspension (400 mg) of washed 175 nm carboxylate modified latex was diluted with 3 mL of ethoxyethanol in a 25 mL round bottom (R.B.) flask with a stir bar. The R.B. flask was then placed in an oil bath at 105° C. and stirred for 10 minutes. Then, 3.3 mM C-28 thioxene and 15.5 mM $Eu(TTA)_3DPP$ was added; the beads were stirred for 5 minutes more. At this point 1.0 mL of 0.1N NaOH was added slowly over 5 minutes. During all the additions, the oil bath temperature was maintained at 105° C. The oil bath temperature was slowly allowed to drop to room temperature over 2 hours. After cooling, the mixture was diluted with 20 mL of ethanol and centrifuged (12,500 rpm, 30 minutes). Supernatants were discarded and the pellets resuspended in ethanol by sonication. Centrifugation was repeated, and the pellet was resuspended in water; and centrifugation was repeated. The pellet was resuspended in 5 mL of aqueous ethanol to a final volume of 40 mL.

Carboxyl acceptor beads prepared above (99 mg in 4.5 mL water) were added slowly with vortexing to 5.5 mL of MAD aminodextran from above, followed by 1 mL of 200 mg/mL NHS in 50 mM MES, pH 6, 1 mL of 200 mg/mL EDAC in water, and 450 µL of 1 M HCl, final pH 6. The mixture was incubated overnight at room temperature in the dark, then reacted with 200 mg succinic anhydride in 0.5 mL of DMSO for 30 min at room temperature. Freshly opened Surfact-Amps Tween-20 (Pierce Chemical Company, Rockford, Ill.) was added and the beads were centrifuged 30 min at 15,000 rpm in a Sorvall RC-5B centrifuge, washed by centrifugation with three 10 mL portions of 50 mM MOPS, 50 mM EDTA, 0.1% Surfact-Amps Tween-20 (Pierce Chemical Company), pH 7.2, and resuspended in 3 mL of the same.

Monoclonal anti-digoxin Ab (prepared as described above) was purified by ABx resin (Baker Chemical Company, Phillipsburg, N.J.) and was dialyzed into 0.15 M NaCl, 5 mM $Na_2HPO_4$, pH 7.4. The anti-digoxin Ab was thiolated by mixing 622 µL (4.28 mg) with 10.2 µL of SATA (1.25 mg/mL in ethanol, 2 eq.), incubating for 1 hr at room temperature and dialyzing cold against 2×2 L of 150 mM NaCl, 10 mM $Na_2HPO_4$, 1 mM EDTA, pH7. The thioacetylated antibody was deacetylated by adding 62.2 µL of hydroxylamine (1 M $H_2NOH$, 50 mM MOPS, 25 mM EDTA, pH 7), bubbling with argon and incubating for 1 hr at room temperature. The product was applied to a Pharmacia PD-10 column (G-25) and eluted with 50 mM MOPS, 50 mM EDTA, pH 7.2, bubbled with argon. After 2.5 mL fore-run, three-1 mL fractions were collected and combined. Recovery of antibody was 3.66 mg or 86% by $A_{280}$. Surfact-Amps Tween-20 (10%) was added to give 0.2% final concentration.

A 1.4 mL aliquot of the thiolated antibody above (1.71 mg antibody) was immediately added to 300 µL (10 mg) of maleimidated beads prepared above plus enough 10% Tween-20 to bring final concentration of the mixture to 0.2%. The tube was purged with argon and incubated overnight at room temperature in the dark. To the above was added 3.4 µL of 1 M $HSCH_2COOH$ in water. After 30 min at room temperature, 6.8 µL of $ICH_2COOH$ (1 M in water) was added. After 30 min 3.5 mL of 0.17M glycine, 0.1M NaCl, 0.1% (v/v) Tween-20, 10 mg/mL BSA, pH 9.2 was added and the beads were centrifuged (30 min at 15,000 rpm), incubated for 3 hr in 5 mL of the same buffer, centrifuged, washed by centrifugation with three-5 mL portions of Buffer C, resuspended in 5 mL of Buffer C and stored under refrigeration. The size of the beads, determined in Buffer C, was 301+/−56 nm. Binding capacity was determined with $^{125}$I-digoxin and was equivalent to 377 antibody molecules per bead.

Silicon tetra-t-butyl phthalocyanine was prepared as follows:

Sodium metal, freshly cut (5.0 g, 208 mmol), was added to 300 mL of anhydrous ether in a two-liter, 3-necked flask equipped with a magnetic stirrer, reflux condenser, a drying tube and a gas bubbler. After the sodium was completely dissolved, 4-t-butyl-1,2-dicyanobenzene (38.64 g, 210 mmol, from TCI Chemicals, Portland Oreg.) was added using a funnel. The mixture became clear and the temperature increased to about 50° C. At this point a continuous stream of anhydrous ammonia gas was introduced through the glass bubbler into the reaction mixture for 1 hr. The reaction mixture was then heated under reflux for 4 hr. while the stream of ammonia gas continued. During the course of the reaction, as solid started to precipitate. The resulting suspension was evaporated to dryness (house vacuum) and the residue was suspended in water (400 mL) and filtered. The solid was dried (60° C., house vacuum, $P_2O_5$). The yield of the product (1,3-diiminoisoindoline, 42.2 g) was almost quantitative. This material was used for the next step without further purification. To a one-liter, three-necked flask equipped with a condenser and a drying tube was added the above product (18 g, 89 mmol) and quinoline (200 mL, Aldrich Chemical Company, St. Louis Mo.). Silicon tetrachloride (11 mL, 95 mmol, Aldrich Chemical Company) was added with a syringe to the stirred solution over a period of 10 minutes. After the addition was completed, the reaction mixture was heated to 180–185° C. in an oil bath for 1 hr. The reaction was allowed to cool to room temperature and concentrated HCl was carefully added to acidify the reaction mixture (pH 5–6). The dark brown reaction mixture was cooled and filtered. The solid was washed with 100 mL of water and dried (house vacuum, 60° C., $P_2O_5$). The solid material was placed in a 1-liter, round bottom flask an concentrated sulfuric acid (500 mL) was added with stirring. The mixture was stirred for 4 hr. at 60° C. and was then carefully diluted with crushed ice (2000 g). The resulting mixture was filtered and the solid wad washed with 100 mL of water and dried. The dark blue solid was transferred to a 1-liter, round bottom flask, concentrated ammonia (500 mL) was added, and the mixture was heated and stirred under reflux for 2 hr., was cooled to room temperature and was filtered. The solid was washed with 50 mL of water and dried under vacuum (house vacuum, 60° C., $P_2O_5$) to give 12 g of product silicon tetra-t-butyl phthalocyanine as a dark blue solid. 3-picoline (12 g, from Aldrich Chemical Company), tri-n-butyl amine (anhydrous, 40 mL) and tri-n-hexyl chlorosilane (11.5 g) were added to 12 g of the above product in a one-liter, three-necked flask, equipped with a magnetic stirrer an a reflux condenser. The mixture was heated under reflux for 1.5 hr. an then cooled to room temperature. The picoline was distilled off under high vacuum (oil pump at about 1 mm Hg) to dryness. The residue was dissolved in $CH_2Cl_2$ and purified using a silica gel column (hexane) to give 10 g of pure product di-(tri-n-hexylsilyl)-silicon tetra-t-butyl phthalocyanine as a dark blue solid. (MS: $[M-H]^+$ 1364.2, absorption spectra: methanol: 674 nm ($\epsilon$ 180,000): toluene 678 nm, $^1$H NMR (250 MHz, $CDCl_3$): 67 : −2.4(m, 12H), −1.3(m, 12H), 0.2–0.9 (m, 54H), 1.8(s, 36H), 8.3(d, 4H) and 9.6 (m, 8H) was consistent with the above expected product.

Sens-Sav—Sensitizer beads coupled to Streptavidin (2300 Sav/bead).

The sensitizer beads were prepared placing 600 mL of carboxylate modified beads (Seradyn) in a three-necked, round-bottom flask equipped with a mechanical stirrer, a glass stopper with a thermometer attached to it in one neck, and a funnel in the opposite neck. The flask had been immersed in an oil bath maintained at 94+/−1° C. The beads were added to the flask through the funnel in the neck and the bead container was rinsed with 830 mL of ethoxyethanol, 1700 mL of ethylene glycol and 60 mL of 0.1N NaOH and the rinse was added to the flask through the funnel. The funnel was replaced with a 24–40 rubber septum. The beads were stirred at 765 rpm at a temperature of 94+/−1° C. for 40 min.

Silicon tetra-t-butyl phthalocyanine (10.0 g) was dissolved in 300 mL of benzyl alcohol at 60+/−5° C. and 85 mL was added to the above round bottom flask through the septum by means of a syringe heated to 120+/−10° C. at a rate of 3 mL per min. The remaining 85 mL of the phthalocyanine solution was then added as described above. The syringe and flask originally containing the phthalocyanine was rinsed with 40 mL of benzyl alcohol and transferred to round-bottom flask. After 15 min 900 mL of deionized water and 75 mL of 0.1N NaOH was added dropwise over 40 min. The temperature of the oil bath was allowed to drop slowly to 40+/−10° C. and stirring was then discontinued. The beads were then filtered through a 43 micron polyester filter and subjected to a Microgon tangential flow filtration apparatus (Microgon Inc., Laguna Hills, Calif.) using ethanol:water, 100:0 to 10:90, and then filtered through a 43 micron polyester filter.

Sulfo-SMCC (11.55 mg) was dissolved in 0.5 mL distilled water. Slowly, during 10 sec, the above solution was added to 5 mL of stirring aminodextran (Molecular Probes, Eugene, Oreg.) solution (12.5 mg/mL in 50 mM MOPS, pH 7.2). The mixture was incubated for 1 hr at room temperature.

To the stirring solution above was added 5 mL of 20 mg/mL (100 mg) of the sensitizer beads prepared above in distilled water. Then, 1 mL of 200 mg/mL NHS (prepared fresh in 50 mM MES, pH adjusted to 6.0 with 6N NaOH). 200 mg EDAC was dissolved in 1 mL distilled water and this solution was added slowly with stirring to the sensitizer beads. The pH was adjusted to 6.0 by addition of 450 µL of 1N HCl and the mixture was incubated overnight in the dark. A solution of 100 mg of succinic anhydride in 0.5 mL of DMSO was added to the sensitizer beads and the mixture was incubated for 30 min at room temperature in the dark. To this mixture was added 0.13 mL 10% Tween-20 bringing the final concentration of Tween-20 to 0.1%. The beads were centrifuged for 45 min at 15,000 rpm as above. The supernatant was discarded and the beads were resuspended in 10 mL of buffer (50 mM MOPS, 50 mM EDTA and 0.1% Tween-20, pH 7.2). The mixture was sonicated to disperse the beads. The beads were centrifuged for 30 min as described above, the supernatant was discarded and the beads were resuspended. This procedure was repeated for a total of three times. Then, the beads were resuspended to 40 mg/mL in 2.5 mL of the above buffer, saturated with argon and Tween-20 was added to a concentration of 0.1%. The beads were stored at 4° C.

Streptavidin was bound to the above beads using 25 mg streptavidin for 100 mg of beads. 25 mg streptavidin (50 mg Aaston solid from Aaston, Wellesley, Mass.) was dissolved in 1 mL of 1 mM EDTA, pH 7.5, and 77 µL of 2.5 mg/mL SATA in ethanol was added thereto. The mixture was incubated for 30 min at room temperature. A deacetylation solution was prepared containing 1M hydroxylamine-HCl, 50 mM Na$_2$PO$_4$, 25 mM EDTA, pH 7.0. 0.1 mL of this deacetylation solution was added to the above solution and incubated for 1 hr at room temperature. The resulting thiolated streptavidin was purified on a Pharmacia PD10 column and washed with a column buffer containing 50 mM MOPS, 50 mM EDTA, pH 7.2. The volume of the sample was brought to 2.5 mL by adding 1.5 mL of the above column buffer. The sample was loaded on the column and eluted with 3.5 mL of the column buffer. The thiolated streptavidin was diluted to 5 mL by adding 1.5 mL of 50 mM MOPS, 50 mM EDTA, 0.1% Tween-20, pH 7.2. 5 mL of the thiolated streptavidin solution was added to 5 mL of the sensitizer beads, under argon, and mixed well. The beads were topped with argon for 1 min, the tube was sealed and the reaction mixture was incubated overnight at room temperature in the dark.

To the above beads was added 7.5 mL of 50 mM MOPS, 50 mM EDTA, 0.1% Tween-20, pH 7.2 to bring the beads to 1 mg/mL. The remaining maleimides were capped by adding mercaptoacetic acid at a final concentration of 2 mM. The mixture was incubated in the dark for 30 min at room temperature. The remaining thiols were capped by adding iodoacetic acid at a final concentration of 10 mM and the mixture was incubated at room temperature for 30 min in the dark. The beads were centrifuged for 30 min at 15,000 rpm as above for a total of three times.

All oligonucleotides, including modified oligonucleotides, were from Oligos Etc., Wilsonville, Oreg.

Genomic DNA having the following point mutations within exon 11 of the CFTR gene used herein:

Heterozygous DNA with one wild type (wt) allele and one of the following mutant alleles:
G542X (G>T substitution) from Roche Molecular Systems, Alameda, Calif.;
G551D (G>A substitution) from Roche Molecular Systems, Alameda, Calif.;
R553X (C>T substitution) from Roche Molecular Systems, Alameda, Calif.;
R560T (G>C substitution) from Roche Molecular Systems, Alameda, Calif.

Example 1

Study of Removal of Modified Nucleotides from the 3'-end of Oligonucleotide Primers This experiment was carried out to demonstrate that (i) the presence of certain unnatural nucleotides at the 3'-end of an oligonucleotide primer prevents it from acting as a primer for amplification such as PCR and (ii) that the unnatural nucleotides can be removed by the 3'-5' exonuclease activity of thermostable Pfu polymerase thus activating the oligonucleotide and allowing it to be extended by a polymerase and to function as a PCR primer.

The following oligonucleotides and modified oligonucleotides were employed in this example:

Oligonucleotide 5'GCCTTTCAAATTCAGATTG-
 AGC 3'(P1) (SEQ ID NO: 1)

Modified oligonucleotides 5'-GCCTTTCAAATTCAGATTGAGC-NN-G-3', where N is:
  a) O-6-methyl deoxy G (P1a) (SEQ ID NO: 2)
  b) O-4-methyl deoxy T (P1b) (SEQ ID NO: 3)
  c) etheno-deoxy A (P1c) (SEQ ID NO: 4)

The oligonucleotide (P1, P1a, P1b or P1c) was diluted to 1.25 μM in 10 mM Tris-HCl (pH 8.3), 50 mM KCl, 4 mM MgCl$_2$, 200 pg/ml BSA (buffer A) and incubated with Pfu polymerase (0.625 U per 50 μl) under conditions mimicking PCR, i.e., incubated with polymerase but not target polynucleotide or dNTP's. Aliquots were withdrawn and chilled on ice after 10, 20, 30 and 40 cycles (30 sec at 94° C., 1 min at 64° C., 1 min at 72° C.). Following this treatment the oligonucleotide was then used as a forward primer in a PCR amplification to amplify a DNA fragment 203 bp in length corresponding to exon 11 of the human cystic fibrosis gene. The compositions of the lower and upper mixes were as follows:

| Lower mix | Volume (μl) | Upper mix | Volume (μl) |
|---|---|---|---|
| H$_2$O | 8 | H$_2$O | 17.25 |
| 10 X buffer A | 2 | 10 X buffer A | 2.5 |
| Σ dNTP (250 μM each) | 4 | Pfu (2.5 U/μl) | 0.25 |
| P1 (P1a, P1b, P1c) (1.25 μM) | 10 | DNA | 5 |
| P2 (12.5 μM) | 1 | (425 bp amplicon, 1:1000) | |

An aliquot of a diluted amplicon 425 bp in length was used as a target polynucleotide. This amplicon was prepared using a WT genomic DNA (Roche Molecular Systems) as a target and primers P1' and P2' below. The hot start procedure using PCR GEM50 wax beads (Perkin Elmer, Norwalk Conn.) was utilized. Wax beads were put in tubes containing the lower mix, the wax was melted and allowed to solidify, and the upper mix was then added. 20 PCR cycles were performed under the same conditions as above. 5 μl aliquots were analyzed in a 4–20% gradient pre-cast gel (Novex, San Diego Calif.). The results obtained indicated that a certain delay in accumulation of the amplicon was observed for all three modified oligonucleotides. P1c appeared to be the most resistant to exonuclease cleavage. The time of delay that was estimated from the gel results was equivalent to less than 10 PCR cycles for P1a and P1b and about 30 PCR cycles for P1c.

All three 3'-modified oligonucleotides were then used in true PCR using genomic DNA. In that regard untreated oligonucleotides P1a, P1b and P1c were added to the reaction mixture. The observed delay in the appearance of the PCR product, as compared to P1, was shorter (equivalent to about 5 PCR cycles) and the difference between the three unnatural bases was much less pronounced, P1a being the least resistant to degradation by the Pfu polymerase.

Example 2

PCR Using Oligonucleotide P1c

This experiment demonstrated that the use of 3'-etheno modified oligonucleotides (P1c and P2c) both as inner primers in nested PCR and by themselves greatly reduced the number of spurious amplification products as determined by gel electrophoresis.

In this experiment both forward (P1c above) and reverse (P2c below) primers contained 3'-etheno modified bases at their 3'-ends.

Primer P2: 5'-GACATTTACAGCAAATG-
 CTTGC-3' (SEQ ID NO: 5)

Primer P2c: 5'-GACATTTACAGCAAATGCTTGC-NN-G-3', where N is etheno-deoxyA (SEQ ID NO: 6)

The outer primers in nested PCR were as follows:

P1' (forward): 5'-CAACTGTGGTTAAAGCAA-
    TAGTGT-3'  (SEQ ID NO:7)

P2' (reverse): 5'-GCACAGATTCTGAGTAACC-
    ATAAT-3'  (SEQ ID NO:8)

The anticipated product from primers P1' and P2' is a product 425 bp in length; the anticipated product from primers P1 and P2 is a product 203 bp in length. The 5'-end of P1 is located 53 nucleotides downstream from the 5'-end of P1'.

In order to encourage non-specific priming (to demonstrate the advantages of the present invention), PCR cycling conditions were deliberately de-optimized by dropping the cycle annealing temperature (from 64° C. as in Example 1 above to 50° C). For the same purpose, PCR was carried out without a hot start. Accordingly, all reaction components were mixed together at room temperature prior to carrying out the PCR reactions. 35 PCR cycles were performed using 50 ng genomic DNA and 0.625 U Pfu polymerase per 50 μl.

The PCR products generated by using 3'-etheno modified oligonucleotides and ordinary or unmodified oligonucleotide primers of the same sequence were analyzed in a 4–20% polyacrylamide gel (Novex). The results obtained are summarized as follows: When unmodified primers were used under suboptimal conditions, several non-specific products were observed in addition to the main band (a strong fast moving band(s) and several slowly moving weak bands). When the 3'-etheno modified oligonucleotides were used, the gel pattern cleared dramatically. The fast moving band and most of the slow moving parasite bands disappeared completely. A possible explanation is that the gradual introduction of functional primers into the PCR reaction as the exonuclease activity of Pfu polymerase cleaves the modified nucleotides from their 3'-ends decreases the chances of false priming at the early stages of PCR, thus improving its overall specificity.

When Taq polymerase was used instead of Pfu, no amplification was observed. This demonstrated that the 3'-5' exonuclease activity present in Pfu polymerase, but absent in Taq polymerase, was responsible for the ultimate removal of unnatural etheno-modified nucleotides.

Example 3

Mutation Detection Using Modified Oligonucleotides and Hot Start

Mutation detection was carried out in accordance with the disclosure in U.S. Patent Application Serial No. 60/009,289 filed Dec. 22, 1995, supra, as described above.

PCR

The hot start procedure using wax beads as described above in Example 1 was employed in this example. Thirty five PCR cycles (30 sec at 94° C., 1 min at 64° C., 1 min at 72° C.) were performed using 50 ng genomic DNA and 0.625 U Pfu polymerase per 50 μl. The hot start procedure using PCR GEM50 wax beads (Perkin Elmer) was utilized. An equimolar mixture of the following primers (total concentration of each forward and reverse primers 250 nM) were used. The primers were chosen because they performed poorly in the mutation detection carried out without the use of the present invention.

Unmodified Primers

P1-Bio: 5'GCCTTTCAAATTCAGATTGAGC 3' (SEQ ID NO: 1) (P1) biotinylated at the 5'-end P1-Dig: forward primer P1 labeled with digoxygenin at the 5'-end P3: a reverse primer having a 3-portion identical with P2 and an additional 5'-"tail" t1 (underlined) 20 nucleotides long:

5'-<u>ACCATGCTCGAGATTACGAGG</u>ACATTA-
   CAGCAAATGCTTGC-3'  (SEQ ID NO: 9)

P4: reverse primer having a 3'-portion identical with P2 and an additional 5'-"tail" t2 (underlined) 20 nucleotides long:

5'-<u>GATCCTAGGCCTCACGTATT</u>GACATTA-
   CAGCAAATGCTTGC-3'  (SEQ ID NO: 10)

3'-etheno Modified Oligonucleotides (Modified Oligos) in Accordance with the Present Invention P1c-Bio (P1c (SEQ ID NO: 4) biotinylated at the 5'end), P1c-Dig (P1c (SEQ ID NO: 4) labeled with digoxygenin at the 5'end), P3c (5'-ACCATGCTCGAGATTACGAGGA-CATTTACAGCAAATGCTTGC-NN-G-3' (SEQ ID NO: 11) where N is etheno-dA) and P4c (5'-GATCC-TAGGCCTCACGTATTGACATTTACAGCAAATGCTT-GC-NN-G-3' (SEQ ID NO: 12) where N is etheno-dA) are the same as P1-Bio, P1-Dig, P3 and P4 but with two etheno-dA's followed by unmodified dG at their 3'-ends. These oligonucleotides were also purchased from Oligos, Etc.

Branch Migration

After completion of PCR as described above, the samples were subjected to branch migration: 95° C., 1 min (denaturation), followed by 65° C., 30 min (branch migration).

Detection

Detection was carried out in a manner similar to that described in U.S. Pat. No. 5,340,716, the relevant portions of which are incorporated herein by reference. Amounts of the components were as follows.

A 2 μl aliquot of the above reaction mixture from the branch migration was mixed with 100 μl of the beads suspension (2.5 μg of Sens-Sav beads and 2.5 μg Acc-Ab$_{Dig}$ beads per 100 μl buffer A), incubated at 37° C. for 5 min. The reaction mixture was then irradiated with a 150 watt Xenon lamp for 3 sec (3 cycles of 1 sec illumination and 1 sec waiting time) and the signal was then read.

The results of a typical experiment conducted according to the protocol of this Example 3 were as follows (Table 1):

TABLE 1

| Invention oligos Sample (RLU) | Control Unmodified primers Signal (RLU) | Modified Signal |
|---|---|---|
| WT1 | 71252 | 6522 |
| WT2 | 75088 | 6186 |
| WT3 | 80016 | 7634 |
| WT4 | 80052 | 6998 |
| G542X/WT heterozygote | 235644 | 576452 |
| G551D/WT heterozygote | 193542 | 426382 |
| R553X/WT heterozygote | 158058 | 390062 |
| R560T/WT heterozygote | 187078 | 440826 |

WT1–4 are wild type homozygotes.

The results obtained demonstrated that the use of 3'-etheno modified oligonucleotides in the branch migration assay resulted in significant improvement over the same assay using unmodified primers not in accordance with the present invention. The wild type signal decreased by an order of magnitude whereas the mutant signal increased by approximately a factor of two with the average signal-to-background ratio increasing from 2.5 (marginal) to 67.

Example 4

Mutation Detection Using Modified Oligonucleotides without Hot Start

In Example 3, the 3'-etheno modified oligonucleotides were aided by implementation of the standard hot start procedure utilizing wax beads. In this Example 4 the hot start procedure employed in Example 3 was not used. PCR conditions were the same as in Example 3, except that all components of the PCR reactions were mixed together at room temperature or on ice. The results are summarized in Table 2.

TABLE 2

|  | Signal (RLU) | | Signal (RLU) | |
| --- | --- | --- | --- | --- |
| Sample | Control Unmodified primers | RT Invention Modified oligos | Control Unmodified primers | Ice Invention Modified oligos |
| WT1 | 97992 | 14988 | 112050 | 8612 |
| WT2 | 112110 | 10566 | 100784 | 9634 |
| G551D/WT | 59828 | 49910 | 99516 | 101016 |
| R553X/WT | 51640 | 45180 | 90592 | 121808 |

When the reactions were assembled at room temperature, the average signal to background ratio of 5.3 was observed with the 3'-etheno modified oligonucleotides as compared to no discrimination between mutant and wild type samples with the unmodified primers (Table 2, left). When the reactions were assembled on ice, the average signal to background ratio increased to 24.2 for the 3'-etheno primers, whereas still no discrimination was observed for the unmodified primers (Table 2, right).

The above results demonstrated that the 3'-5' exonuclease activity of the Pfu polymerase was occurring at room temperature and removed the modified nucleotides from some of the molecules of the modified oligonucleotides before PCR cycling began. To slow this process down, smaller amounts of Pfu polymerase were used. In order to preserve the efficiency and yield of PCR, Pfu polymerase was supplemented with Pfu exo (from Stratagene, La Jolla Calif.) in which the 3'-5' exonuclease activity is missing. PCR conditions were the same as above, except that 40 cycles were performed. The total amount of polymerase (Pfu+Pfu exo⁻) per reaction was 0.625 U. To make the conditions maximally unfavorable (to encourage non-specific priming), PCR reactions containing 3'-etheno modified oligonucleotides were left at RT for as long as 30 min prior to starting thermocycling. The results are summarized in Table 3.

TABLE 3

|  | Signal (RLU) | | |
| --- | --- | --- | --- |
| Sample | Pfu | Pfu exo-/Pfu (2:1) | Pfu exo-/Pfu (1:1) |
| WT1 | 18970 | 8704 | 14540 |
| WT2 | 18652 | 9234 | 21656 |
| G551D/WT | 103236 | 173964 | 314368 |
| R553X/WT | 75130 | 210706 | 337192 |

The results summarized in Table 3 demonstrated that, when the mixture of two enzymes (Pfu and Pfu exo⁻) was used, the 3'-etheno primers were very effective as judged by a signal to background ratio of about 20 as compared with a signal to background ratio of about 4.5 for Pfu alone.

By employing the method of the present invention in conjunction with the mutation detection, a substantial improvement of the signal-to-background ratio in a direct approach as applied to the detection of 4 point mutations in exon 11 of the human CFTR gene was realized as demonstrated by this Example 5. The approach of the present invention as applied to the above mutation detection method achieves at least the same results as the known hot start method using wax beads.

The above discussion includes certain theories as to mechanisms involved in the present invention. These theories should not be construed to limit the present invention in any way, since it has been demonstrated that the present invention achieves the results described.

The above description and examples fully disclose the invention including preferred embodiments thereof. Modifications of the methods described that are obvious to those of ordinary skill in the art such as molecular biology and related sciences are intended to be within the scope of the following claims.

What is claimed is:

1. A method for selectively extending an oligonucleotide primer along a specific target polynucleotide sequence in a mixture of polynucleotides, said method comprising:
   (a) providing in combination said mixture and a modified oligonucleotide having a 3'-end that is inefficiently extendable in a template dependent manner along any polynucleotide sequence; and
   (b) controlling the template dependent extension of said oligonucleotide primer along said specific target polynucleotide sequence by controlling the degradation of said 3'-end of said modified oligonucleotide thereby producing said oligonucleotide primer.

2. The method of claim 1 wherein said degradation is enzymatically catalyzed.

3. The method of claim 1 wherein said modified oligonucleotide comprises one or more nucleotide analogs at said 3'-end that inhibit chain extension of said modified oligonucleotide along all polynucleotides in said mixture.

4. The method of claim 3 wherein said one or more nucleotide analogs hybridize inefficiently to any normal nucleotide in a polynucleotide.

5. In a template dependent method for amplifying a target polynucleotide sequence, said method comprising combining said target polynucleotide sequence with reagents for amplifying said target polynucleotide sequence and subjecting said combination to conditions wherein said target polynucleotide sequence is amplified in a template dependent manner, said reagents comprising an oligonucleotide primer and a polymerase, the improvement which comprises said oligonucleotide prime being derived from a modified oligonucleotide having a portion that hybridizes to said target polynucleotide sequence except for the 3'-end thereof, said 3'-end having at least one nucleotide analog that is substantially incapable of hybridizing to a polynucleotide, said 3'-end being degradable to provide said oligonucleotide primer.

6. The method of claim 5 wherein said modified oligonucleotide has a 3'-end that comprises at least two unnatural nucleotides that do not hybridize to said target polynucleotide sequence.

7. The method of claim 5 wherein said at least one nucleotide analogue is a natural nucleotide having a chemical modification that is removeable.

8. The method of claim 5 wherein said nucleotide analog is removable by an enzyme having 3' to 5' exonuclease activity.

9. The method of claim 7 wherein said chemical modification is selected from the group consisting of esters, glycosides, sulfates and amides.

10. A method for amplifying a target polynucleotide sequence, which comprises:
    (a) providing in combination (i) said target polynucleotide sequence and (ii) reagents for conducting a template dependent amplification of said target polynucleotide sequence, said reagents comprising a polymerase, nucleoside triphosphates and a modified oligonucleotide comprising at least one nucleotide analog at the 3'-end thereof, said nucleotide analog being substantially non-hyridizable to any polynucleotide sequence and being removable by a 3' to 5' exonuclease at a rate that is slower than for a natural nucleotide.
    (b) subjecting said combination to conditions for amplifying said target polynucleotide sequence in a template dependent manner, wherein said nucleotide analog is removed from said modified oligonucleotide to give an oligonucleotide primer, which is then extended along said target polynucleotide sequence to produce an extended oligonucleotide primer.

11. The method of claim 10 which comprises detecting said target polynucleotide sequence by detecting said extended oligonucleotide primer.

12. The method of claim 10 wherein said reagents comprise a second modified oligonucleotide that is degradable to a second oligonucleotide primer.

13. The method of claim 10 wherein said nucleotide analog has a 3'-hydroxyl group.

14. The method of claim 10 wherein said nucleotide analog is a natural nucleotide having a chemical modification that is removable.

15. The method of claim 10 wherein said nucleotide analog is removable by an enzyme having 3' to 5' exonuclease activity.

16. The method of claim 14 wherein said chemical modification is selected from the group consisting of esters, glycosides, sulfates and amides.

17. The method of claim 10 wherein said nucleotide analog is at the 3'-terminus of said modified oligonucleotide.

18. The method of claim 10 wherein said nucleotide analog is within one nucleotide of the 3'-terminus of said modified oligonucleotide.

19. The method of claim 10 wherein said nucleotide analog is attached directly to a sequence of 12 to 50 nucleotides of said modified oligonucleotide that hybridize to said target polynucleotide sequence.

20. The method of claim 10 wherein said nucleotide analog is comprised of an unnatural base selected from the group consisting of adenine modified at the 6-amino group, guanine modified at the 6-oxygen, thymine modified at the 4-oxygen, purines modified at the ring nitrogens at the 5-position, pyrimidines modified at the ring nitrogens at the 3-position, guanine modified by removal of the 2-amino group and cytosine modified by the removal of the 4-amino group.

21. The method of claim 10 wherein said target polynucleotide is DNA.

22. In a template dependent method for amplifying a target polynucleotide sequence, said method comprising combining said target polynucleotide sequence with reagents for amplifying said target polynucleotide sequence and subjecting said combination to conditions wherein said target polynucleotide sequence is amplified in a template dependent manner, said reagents comprising an oligonucleotide primer and a polymerase, the improvement which comprises said oligonucleotide primer being derived from a modified oligonucleotide having a portion that hybridizes to said target polynucleotide sequence except for the 3'-end thereof, said 3'-end being degradable at a rate of degradation of said oligonucleotide primer hybridized to said target polynucleotide sequence is slow relative to the rate of degradation of said 3'-end of non-hybridized oligonucleotide primer.

23. In a method for forming multiple copies of a target polynucleotide sequence, said method comprising:
  (a) hybridizing to the 3'-end of said target sequence a first oligonucleotide primer ("first primer"),
  (b) extending in a template dependent manner in the presence of a polymerase, said first primer along at least said target sequence, said first primer being capable of hybridizing to, and being extended along, (1) said extended first primer or (2) an extended second oligonucleotide primer ("second primer") wherein said extended second primer results from the extension of a second primer capable of hybridizing to and extending along a polynucleotide that is complementary (complementary polynucleotide) to said target sequence,
  (c) dissociating said extended first primer from said target sequence,
  (d) hybridizing, to the 3'-end of said extended first primer, said first or said second primer,
  (e) extending said first or said second primer along said extended first primer,
  (f) dissociating said extended first primer or said extended second primer from said extended first primer,
  (g) hybridizing, to the 3'-end of said extended first or second primer, said first primer, and
  (h) repeating steps (e)–(g),
the improvement comprising said first oligonucleotide primer being derived from a modified oligonucleotide having a portion that hybridizes to said target polynucleotide sequence except for the 3'-end thereof, said 3'-end having at least one nucleotide analog, said nucleotide analog comprising at least one natural nucleotide having a chemical modification that is removable, said nucleotide analog further being incapable of hybridizing to a polynucleotide, whereby said extension steps (b) and (h) are controlled by the removal of said chemical modification or said analog.

24. The method of claim 23 wherein said modified oligonucleotide has a 3'-end that comprises at least two unnatural nucleotides that do not hybridize to said target polynucleotide sequence.

25. The method of claim 23 wherein said nucleotide analog is removable by an enzyme having 3' to 5' exonuclease activity.

26. The method of claim 23 wherein said chemical modification is selected from the group consisting of esters, glycosides, sulfates and amides.

27. The method of claim 23 wherein the presence of said extended first primer and/or said extended second primer is detected and related to the presence of said target polynucleotide.

28. The method of claim 23 wherein the repeating of steps (e)–(g) is achieved by repeated temperature cycling.

29. The method of claim 28 wherein temperature cycling is repeated at least 3 times.

30. The method of claim 23 wherein said target polynucleotide is DNA.

31. The method of claim 23 wherein said extending is carried out in the presence of nucleoside triphosphates.

32. The method of claim 23 wherein said first and said second primers are different.

33. The method of claim 23 wherein said first and said second primers are different and said extended first primer is a template for said second primer and said extended second primer is a template for said first primer.

34. A method for controlling the concentration of an oligonucleotide primer in a reaction medium for conducting a reaction in which said oligonucleotide primer is extended along a polynucleotide template, said method comprising:
  (a) providing in said reaction medium, together with reactants for extending said oligonucleotide primer along said polynucleotide template in a template dependent manner, a modified oligonucleotide having a degradable 3'-end, said modified oligonucleotide being substantially incapable of being extended along said polynucleotide template, wherein the degradation of said 3'-end results in the formation of said oligonucleotide primer and
  (b) subjecting said reaction medium to controlled conditions for degrading said 3'-end of said modified oligonucleotide thereby forming said oligonucleotide primer.

35. The method of claim 34 wherein said 3'-end comprises at least one nucleotide analog that is incapable of hybridizing with a natural nucleotide.

* * * * *